(12) United States Patent
Yeo et al.

(10) Patent No.: US 9,976,954 B2
(45) Date of Patent: May 22, 2018

(54) MICROFLUIDIC DEVICE AND METHOD OF DETECTING SAMPLE SUPPLIED TO THE SAME

(71) Applicant: SAMSUNG ELECTRONICS CO., LTD., Suwon-si (KR)

(72) Inventors: Yeong Bae Yeo, Seoul (KR); Jung Ki Min, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 14/855,704

(22) Filed: Sep. 16, 2015

(65) Prior Publication Data

US 2016/0187257 A1    Jun. 30, 2016

(30) Foreign Application Priority Data

Dec. 30, 2014   (KR) .................. 10-2014-0194090

(51) Int. Cl.
*G01N 21/03*   (2006.01)
*G01N 21/75*   (2006.01)
(Continued)

(52) U.S. Cl.
CPC ........ *G01N 21/5907* (2013.01); *B01L 3/5027* (2013.01); *B01L 3/502715* (2013.01); *B01L 2200/0605* (2013.01); *B01L 2200/14* (2013.01); *B01L 2200/143* (2013.01); *B01L 2300/0627* (2013.01); *B01L 2300/0654* (2013.01); *B01L 2300/0803* (2013.01); *B01L 2300/087* (2013.01); *B01L 2300/0864* (2013.01);
(Continued)

(58) Field of Classification Search
CPC .......... G01N 1/00; G01N 33/00; G01N 21/03; G01N 21/75; F16K 3/00; B01L 3/00
USPC ......... 422/68.1, 502, 503, 504; 436/43, 164, 436/180, 165; 73/64.56, 863; 137/803, 137/833
See application file for complete search history.

(56) References Cited

U.S. PATENT DOCUMENTS 5,130,258 A    7/1992   Makino et al.
6,100,541 A    8/2000   Nagle et al.
(Continued)

FOREIGN PATENT DOCUMENTS

EP           2165764 A1     3/2010
EP           2684608 A2     1/2014
KR     10-2010-0034311 A    4/2010

OTHER PUBLICATIONS

Communication dated May 9, 2016, issued by the European Patent Office in counterpart European Patent Application No. 15193119.3.
(Continued)

*Primary Examiner* — Brian J Sines
(74) *Attorney, Agent, or Firm* — Sughrue Mion, PLLC

(57) ABSTRACT

A microfluidic device includes a chamber configured to accommodate a sample and air, and a detection device provided with a light emitter configured to emit light towards the chamber on a light transmission path and a light receiver configured to receive the light, and further configured to measure an optical density of the chamber to determine whether the sample is accommodated in the chamber based on the received light. A boundary between the sample and the air accommodated in the chamber is provided on the light transmission path.

8 Claims, 25 Drawing Sheets

(51) Int. Cl.
  *G01N 21/59* (2006.01)
  *B01L 3/00* (2006.01)
(52) U.S. Cl.
  CPC .............. *B01L 2300/0867* (2013.01); *B01L 2300/0877* (2013.01); *B01L 2300/161* (2013.01); *B01L 2300/165* (2013.01); *B01L 2300/168* (2013.01); *B01L 2400/0409* (2013.01); *B01L 2400/0677* (2013.01); *G01N 2021/5969* (2013.01)

(56) References Cited

U.S. PATENT DOCUMENTS

| | | | | |
|---|---|---|---|---|
| 6,803,019 | B1 * | 10/2004 | Bjornson | G01N 27/44791 422/504 |
| 6,900,021 | B1 * | 5/2005 | Harrison | B01J 19/0093 422/504 |
| 8,327,726 | B2 | 12/2012 | Kim et al. | |
| 8,539,823 | B2 | 9/2013 | Lee | |
| 2004/0086427 | A1 * | 5/2004 | Childers | B01L 3/502707 422/400 |
| 2004/0189311 | A1 * | 9/2004 | Glezer | B01J 19/0046 324/444 |
| 2008/0156079 | A1 | 7/2008 | Momose | |
| 2009/0068726 | A1 | 3/2009 | Magnin et al. | |
| 2009/0111675 | A1 | 4/2009 | Yokogawa et al. | |
| 2010/0081213 | A1 | 4/2010 | Lee et al. | |
| 2010/0093105 | A1 | 4/2010 | Lee et al. | |
| 2012/0293796 | A1 | 11/2012 | Ludowise et al. | |
| 2013/0029361 | A1 * | 1/2013 | Hamachi | B01L 3/50273 435/7.92 |
| 2013/0112296 | A1 | 5/2013 | Lee et al. | |

OTHER PUBLICATIONS

International Search Report [PCT/ISA/210] dated Oct. 29, 2015 issued in International Application No. PCT/KR2015/009401.

* cited by examiner

MICROFLUIDIC DEVICE AND METHOD OF DETECTING SAMPLE SUPPLIED TO THE SAME

CROSS-REFERENCE TO RELATED APPLICATION

This application claims priority from Korean Patent Application No. 10-2014-0194090, filed on Dec. 30, 2014 in the Korean Intellectual Property Office, the disclosure of which is incorporated herein by reference in its entirety.

BACKGROUND

1. Field

Apparatuses and methods consistent with exemplary embodiments relate to a microfluidic device and a method of detecting a sample supplied to the same, and more particularly, a microfluidic device having an improved structure capable of determining whether an appropriate amount of sample is inserted or not, and a method of detecting a sample supplied to the same.

2. Description of the Related Art

Various methods for analyzing samples have been developed in various fields of application, such as environmental monitoring, food inspection, and medical diagnostic field, but related art test methods require a significant amount of manual labor and various devices. In order to perform a test according to a defined protocol, a skilled experimenter should proceed with a variety of steps, such as performing a number of reagent injections, mixing, separation and moving, reaction, and centrifugation, and this test method may become a critical cause of inducing errors in the test results.

In order to perform the test quickly, skilled medical technologists are needed. However, there may be difficulties for the skilled medical technologist to run several tests at the same time. In the diagnosis of an emergency, rapid test results are very important to provide fast first aid. Thus, an apparatus may be needed that is capable of rapidly and accurately performing a number of pathological tests required according to situations, at the same time.

In the related art pathological tests, large and expensive automatic apparatuses may be used, and a sample, such as a relatively large amount of blood, may be needed. In addition, it may take a lot of time, e.g., from 2~3 days to 1~2 weeks, to obtain the results after samples are taken from the patient.

To relieve these difficulties, a miniaturized and automated apparatus capable of analyzing a sample taken from one patient or a small number of patients quickly as needed may be used. For example, blood is inserted into a disc type microfluidic device, and serum is separated from blood by the centrifugal force generated by the rotation of the microfluidic device. The separated serum is mixed with a certain amount of diluent, and then moved to a plurality of reaction chambers in the disc type microfluidic device. In the plurality of reaction chambers, different reagents different from each other according to blood test items are injected in advance, and thus, the reagent makes a color by reacting with the serum. By detecting the change of the color, the blood analysis may be performed.

When an amount of a sample injected into a microfluidic device is insufficient, it may be difficult to perform centrifugation and metering and thus the wrong test results may be calculated. Therefore, whether the amount of a sample injected into the microfluidic device is sufficient may enormously influence the test results. For example, whether the amount of a sample injected into the microfluidic device is sufficient may be confirmed by measuring the optical density. In general, when an amount of a sample is sufficient, the optical density may be measured to be higher than the reference optical density, and when the amount of a sample is insufficient, the optical density may be measured to be lower than the reference optical density. However, although the amount of a sample is sufficient, the optical density may be measured to be lower than the reference optical density and thus it may be determined that the amount of a sample is insufficient.

SUMMARY

Therefore, it is an aspect of the exemplary embodiments to provide a microfluidic device provided with an improved structure capable of determining whether a sample is sufficiently injected regardless of the type of the sample, and a method of detecting a sample supplied to the same.

Additional aspects of the exemplary embodiments will be set forth in part in the description which follows and, in part, will be obvious from the description, or may be learned by practice of the exemplary embodiments.

In accordance with an aspect of an exemplary embodiment, a microfluidic device includes a chamber configured to accommodate a sample and air, and a detection device provided with a light emitter configured to emit light towards the chamber on a light transmission path and a light receiver configured to receive the light, and further configured to measure an optical density of the chamber to determine whether the sample is accommodated in the chamber based on the received light, wherein a boundary between the sample and the air accommodated in the chamber is provided on the light transmission path.

The microfluidic device may further include a platform, a sample chamber provided inside the platform and configured to receive the sample, and a sample distribution chamber provided on a side of the sample chamber in a radial direction of the platform and configured to be supplied with the sample accommodated in the sample chamber, wherein the chamber may be connected to the sample distribution chamber to be supplied with the sample accommodated in the sample distribution chamber.

The microfluidic device may further include a sample accommodating chamber provided on a side of the chamber and connected to the chamber, the platform may be rotatably disposed, and the microfluidic device may further include a sample moving channel configured to connect the chamber to the sample accommodating chamber.

The chamber may include a channel connected to the sample distribution chamber to enable a sample accommodated in the sample distribution chamber to flow out of the sample distribution chamber, and an accommodation unit connected to the channel to accommodate a sample which passes through the channel and provided on a side of the channel in a radial direction of the platform, wherein the sample moving channel may connect the accommodation unit to the sample accommodating chamber so that a part of the sample accommodated in the accommodation unit is moved to the sample accommodating chamber.

The accommodation unit may include a first accommodation unit provided on an outer side of the sample moving channel in the radial direction of the platform and a second accommodation unit provided on an inner side of the sample moving channel in the radial direction of the platform and provided to face the channel, wherein the first accommodation unit may be filled with the sample and the second accommodation unit is filled with the air.

The chamber may include an inner surface which is one of a hydrophilic material and a hydrophobic material.

The chamber may include a surface facing the light emitter, a first surface opposite to a surface facing the light emitter, a surface facing the light receiver, and a second surface opposite to the surface facing the light receiver, wherein the first surface and the second surface may be at least one of a hydrophilic material and a hydrophobic material.

The sample may fill a portion of the chamber.

The platform may be rotatably provided, and the sample distribution chamber may include a first collector configured to accommodate, by centrifugation of the microfluidic device, a material having a low density from the sample, and a second collector configured to accommodate, by centrifugation of the microfluidic device, a material having a high density from the sample, the high density being higher than the low density, wherein the chamber may be connected to the first collector.

The light emitter may include at least one of a photodiode and a recording device.

A dye may be provided inside the chamber to dye the sample introduced into the chamber.

In accordance with another aspect of an exemplary embodiment, a method of detecting a sample to determine whether an amount of the sample supplied to a microfluidic device is appropriate includes moving a remaining portion of the sample, which is remaining after filling a sample distribution chamber with the sample, to an excess sample chamber, moving a part of the remaining portion of the sample moved to the excess sample chamber to a sample accommodating chamber so that a portion of the excess sample chamber is filled with the sample, and measuring an optical density of the excess sample chamber by using a detection device.

The detection device may include a light emitter configured to emit light towards the excess sample chamber on a light transmission path and a light receiver configured to receive the light and measure an optical density of the excess sample chamber based on the received light.

A boundary between the part of the remaining portion of the sample and air accommodated in the chamber may be provided on the light transmission path.

The excess sample chamber may include a first plate facing the light emitter and a second plate facing the light receiver, wherein the first plate and the second plate include one of a hydrophilic material and hydrophobic material.

The excess sample chamber and the sample accommodating chamber may be connected to an excess sample moving channel.

The method may further include dyeing a sample introduced into the excess sample chamber.

In accordance with another aspect of an exemplary embodiment, a microfluidic device includes a chamber configured to accommodate a sample, and a detection device provided with a light emitter configured to emit light towards the chamber on a light transmission path and a light receiver configured to receive the light and measure an optical density of the chamber to confirm whether the sample is accommodated in the chamber, and a structure, formed in the chamber, configured to change a direction of the light along the light transmission path The structure may include a concave-convex structure formed on an inner wall of the chamber.

The chamber may include a first chamber, and a second chamber provided with the concave-convex structure formed on the inner wall thereof.

The first chamber and the second chamber may be connected to each other so that the sample may be enabled to move between the first chamber and the second chamber.

The microfluidic device may further include a platform in which the chamber is provided, a sample chamber provided inside the chamber in a radial direction of the platform, the sample chamber being configured to receive the sample, and a sample distribution chamber provided on a side of the sample chamber in the radial direction of the platform and configured to be supplied with the sample accommodated in the sample chamber, wherein the chamber may be connected to the sample distribution chamber to be supplied with the sample accommodated in the sample distribution chamber.

The chamber may further include a channel configured to connect at least one of the first chamber and the second chamber to the sample distribution chamber so that a sample accommodated in the sample distribution chamber may be enabled to move to the at least one of the first chamber and the second chamber.

The channel may be divided to be connected to the first chamber and the second chamber.

The chamber may include an inclined surface inclined to the direction of the light along the light transmission path.

The inclined surface is inclined so that the light emitted from the light emitter may be totally reflected.

The chamber may include a first chamber and a second chamber on which the inclined surface may be formed, the second chamber being connected to the first chamber so that the sample may be enabled to move to the first chamber.

The chamber may include a surface facing the light emitter, a first surface opposite to the surface facing the light emitter, a surface facing the light receiver, and a second surface opposite to the surface facing the light receiver, wherein the structure configured to change the direction of the light may be formed on at least one of the first surface and the second surface.

In accordance with another aspect of an exemplary embodiment, a method of detecting a sample to determine whether an amount of the sample supplied to a microfluidic device is appropriate includes injecting the sample into a sample chamber, moving the sample injected into the sample chamber to a sample distribution chamber, moving a remaining portion of the sample, which is remaining after filling the sample distribution chamber, to an excess sample chamber including a first area and a second area, measuring an optical density of the first area and the second area by using a detection device, and determining that an appropriate amount of the sample is supplied to the microfluidic device when the optical density of the first area is higher than a reference optical density or when the optical density of the second area is lower than the reference optical density.

The detection device may include a light emitter configured to emit light towards the chamber along a light transmission path and a light receiver configured to receive the light and measure the optical density of the excess sample chamber based on the received light.

A structure configured to change the direction of the light along the light transmission path may be formed in the second area.

A concave-convex structure may be formed on an inner wall of the second area.

The second area may include an inclined surface inclined to the direction of the light.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1:
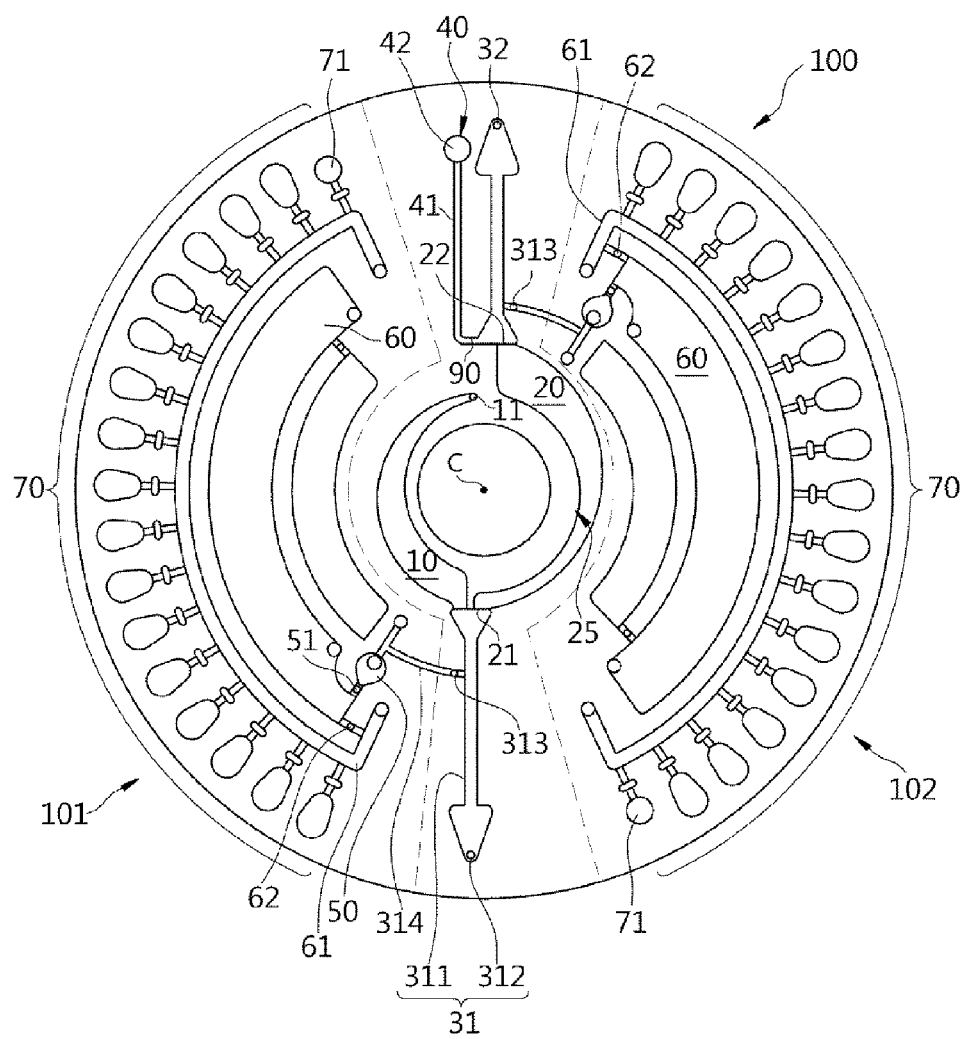
FIG. 1 is a view illustrating a microfluidic device in accordance with an exemplary embodiment.

Reference will now be made in detail to the exemplary embodiments of the present disclosure, examples of which are illustrated in the accompanying drawings, wherein like reference numerals refer to like elements throughout. In addition, terms such as, "front end", "rear end", "upper portion", "lower portion", "upper end", and "lower end" are defined with respect to the drawings, and the shape and the position of the components are not limited to the terms. Hereinafter, reference numeral S may represent a sample.

FIG. 1 is a view illustrating a microfluidic device in accordance with an exemplary embodiment. Hereinafter, a sample may be formed in a way that a fluid and material in the shape of a particle having higher density than that of the fluid are mixed. For example, a biological sample, such as blood, salvia, urine, etc., may be used. Hereinafter, an excess sample chamber 40 may be a type of a chamber.

As illustrated in FIG. 1, a microfluidic device may include a platform 100, and microfluidic structures provided with a space where fluids are accommodated and a flow path where fluids flow.

The platform 100 may be disposed to be rotatable. The platform 100 may be rotatable with respect to a rotation axis C. That is, the microfluidic device may be rotatable to be mounted to a rotation driving unit 510 (e.g., rotation driver) (refer to FIG. 3). In this case, in the microfluidic structures disposed inside the platform 100, the movement and the mixture of sample may be performed by the centrifugal force by the rotation of the platform 100.

For example, the platform 100 may have the shape of a disc.

The platform 100 may be formed of plastic material, such as acrylic, and polydimethylsiloxane (PDMS), which is easily formed and has a surface which is chemically and biologically inactive. However, materials forming the platform 100 are not limited thereto, and any material having chemical and biological stability, optical transparency and mechanical processability may be used in accordance with an exemplary embodiment.

The platform 100 may be formed with a plurality of plates. An intaglio structure corresponding to the microfluidic structure, such as a chamber or a channel, is formed on a surface on which two plates contact each other, and the two plates are bonded to each other so that a space and a path may be formed in the platform 100.

For example, the platform 100 may have a structure including a first substrate (not shown) and a second substrate (not shown) mounted to the first substrate. Alternatively, the structure may include a division plate (not shown) provided between the first substrate and the second substrate, and configured to define a chamber in which a fluid may be accommodated and a channel on which the fluid may flow. The shape of the platform 100 is not limited thereto. The first substrate and the second substrate may be formed of thermo plastic resin.

Bonding of the first substrate and the second substrate may be performed using one of various methods, such as adhesion by using an adhesive or a double-sided adhesive tape, ultrasonic fusion, or laser welding.

Hereinafter, microfluidic structures disposed in the platform 100 to test a sample will be described. An adjacent portion to the rotation axis C in a radial direction of the platform 100 may be referred to as an "inner side" and a far portion to the rotation axis C in a radial direction of the platform 100 may be referred to as an "outer side".

The microfluidic structures may include a sample chamber 10. The sample chamber 10 may be disposed in the most inner side of the platform 100. A sample may be inserted to the sample chamber 10. In the sample chamber 10, a sample inlet 11 may be provided to insert a sample.

The microfluidic structures may further include at least one sample distribution chamber 31 and 32 to be supplied with a sample accommodated in the sample chamber 10. At least one of the sample distribution chambers 31 and 32 may be disposed on an outer side of the sample chamber 10 in the radial direction of the platform 100. The at least one of the sample distribution chambers 31 and 32 may be provided to supply a sample supplied from the sample chamber 10 to at least one of an analysis chamber 101 and 102. The at least one of the sample distribution chambers 31 and 32 may include a first sample distribution chamber 31 and a second sample distribution chamber 32. The first sample distribution chamber 31 and the second sample distribution chamber 32 may have a certain capacity to measure an appropriate amount of sample required for a test. In a process of transmitting a sample from the sample chamber 10 to the first sample distribution chamber 31 and the second sample distribution chamber 32, the centrifugal force generated by the rotation of the platform 100 may be used. Therefore, the first sample distribution chamber 31 and the second sample distribution chamber 32 may be disposed in an outer side as compared to a side at which the sample chamber 10 is disposed.

The at least one of the sample distribution chambers 31 and 32 may have a structure to perform centrifugation of a sample. In other words, at least one of the first sample distribution chamber 31 and the second sample distribution chamber 32 may have a structure to perform centrifugation of a sample. For example, the first sample distribution chamber 31 may act as a centrifuge to divide a sample, e.g., blood, into supernatant and sediment by using the rotation of the platform 100. The first sample distribution chamber 31 may include a first collection unit 311 (e.g., first collector) and a second collection unit 312 (e.g., second collector). Material having a low density in the sample may be accommodated in the first collection unit 311 by the centrifugation. Material having a high density in the sample may be accommodated in the second collection unit 312 by the centrifugation. The first collection unit 311 may have the shape of a channel extended in the radial direction of the platform 100. The second collection unit 312 may be provided in one end portion of the first collection unit 311 to provide a space in which material having large specific gravity is accommodated. Particularly, the second collection unit 312 may be provided in one end portion of the first collection unit 311 to be disposed in an outer side of the first collection unit 311 in the radial direction of the platform 100. According to this configuration, test items that require centrifugation and test items that do not require centrifugation may be tested by a single microfluidic device. Hereinafter, a case where a structure capable of performing centrifugation of a sample is applied to both of the first sample distribution chamber 31 and the second sample distribution chamber 32, will be described. That is, the first sample distribution chamber 31 and the second sample distribution chamber 32 may include the first collection unit 311 and the second collection 312, respectively.

The first sample distribution chamber 31 may be directly connected to the sample chamber 10 to be supplied with a sample. The second sample distribution chamber 32 may be connected the first sample distribution chamber 31 via a sample conveying unit 20 (e.g., sample conveyor). A sample supplied from the sample chamber 10 to the first sample distribution chamber 32 fills the first sample distribution chamber 31, and then fills the second sample distribution chamber 32 via the sample conveying unit 20.

The sample conveying unit 20 may form a sample movement path. The sample conveying unit 20 may include a first connection unit 21 (e.g., first connector) connected to the first sample distribution chamber 31 and a second connection unit 22 (e.g., second connector) connected to the second sample distribution chamber 32. The first connection unit 21 and the second connection unit 22 may be provided on an outer wall 25 of the sample conveying unit 20. When the platform 100 is rotated, a sample may be moved to the first sample distribution unit 31 by the centrifugal force to fill the first sample distribution unit 31 and then moved to the sample conveying unit 20. The sample may flow along the outer wall 25 of the sample conveying unit 20 by the centrifugal force and then move to the second sample distribution chamber 32 via the second connection unit 22.

The microfluidic structures may further include the excess sample chamber 40. The excess sample chamber 40 may be provided inside the platform 100 to accommodate a sample. The excess sample chamber 40 may be connected to at least one sample distribution chamber 31 and 32 to be supplied with a sample accommodated in the at least one sample distribution chamber 31 and 32. The excess sample chamber 40 may be connected to the first collection unit 311 of at least one sample distribution chamber 31 and 32. Particularly, the excess sample chamber 40 may be connected to the second sample distribution chamber 32 via a connection channel 90. A remaining sample after filling the second sample distribution chamber 32 may be moved to the excess sample chamber 40 via a connection channel 90.

The description of the excess sample chamber 40 will be described later.

The microfluidic structures may further include at least one analysis chamber 101 and 102. The at least one analysis chamber 101 and 102 may include a first analysis chamber 101 and a second analysis chamber 102. The first analysis chamber 101 and the second analysis chamber 102 may be a chamber configured to test test-items that require different dilution ratios from each other. For example, among blood test items, Albumin (ALB), Alanine Phosphatase (ALP), Amylase (AMY), Urea Nitrogen (BUN), calcium (Ca++), Total Cholesterol (CHOL), Chloride (Cl−), Creatinine (CRE), Glucose (GLU), High-Density Lipoprotein cholesterol (HDL), Potassium (K+), Lactate Dehydrogenase (LD), Sodium (Na+), Total Bilirubin (T-BIL), Total Protein (TP), Triglycerides (TRIG), and Uric Acid (UA) require that a dilution ratio of serum and diluent is 1:100. In addition, alanine aminotransferase (ALT), aspartate aminotransferase (AST), Creatin Kinase (CK), Direct Bilirubin (D-BIL), and Gamma Glutamyl Transferase (GGT) require that a dilution ratio of serum and diluent is 1:20. Therefore, the first analysis chamber 101 may be a chamber to test test-items that require that a dilution ratio of serum and diluent is 1:100, and the second analysis chamber 102 may be a chamber to inspect test items that require that a dilution ratio of serum and diluent is 1:20. It is understood that these dilution ratios are exemplary only.

Alternatively, the first analysis chamber 101 and the second analysis chamber 102 may be a chamber to test test-items that require the same dilution ratio.

Alternatively, the first analysis chamber 101 may be a chamber to test test-items that require centrifugation, and the second analysis chamber 102 may be a chamber to test test-items that do not require centrifugation. Conversely, the first analysis chamber 101 may be a chamber to test test-items that do not require centrifugation, and the second analysis chamber 102 may be a chamber to test test-items that require centrifugation.

At least one analysis chamber 101 and 102 may be formed to accommodate the same amount of test-items. However, the analysis chambers 101 and 102 are not limited thereto, and when differing amounts of diluent or reagent are required depending on test-items, the analysis chambers 101 and 102 may be formed to have different capacities from each other.

The first analysis chamber 101 and the second analysis chamber 102 may have practically the same structure, and thus, hereinafter the first analysis chamber 101 will be primarily described.

A sample distribution channel 314 configured to distribute collected supernatant (e.g., serum when blood is used as a sample) to a microfluidic structure of the next step may be disposed in one side of the first collection unit 311. The sample distribution channel 314 may be connected to the first connection unit 311 via a valve 313.

The microfluidic structures may further include the valve 313. The valve 313 may include a variety of microfluidic valves. For example, the valve 313 may include a valve which is passively opened when a larger pressure than a certain level is applied, and a valve which is actively operated by receiving a driving force or energy from the outside by an operation signal.

The valve 313 may be a valve that is initially closed to close the sample distribution channel 314 to prevent a fluid to flow before absorbing electromagnetic wave energy.

A material of the valve 313 may employ thermo plastic resin, such as cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), and polyvinylidene fluoride (PVDF).

In addition, the valve material may employ phase change material that is a solid state at room temperature. The phase change material may be injected into the sample distribution channel 314 in a molten state, and then block the sample distribution channel 314 by being solidified. The phase change material may be wax. When heated, wax is changed to a liquid state by melting, and the volume is expanded. For example, paraffin wax, microcrystalline wax, synthetic wax, or natural wax may be employed. The phase change material may be gel or thermo plastic resin. The gel may include polyacrylamide, polyacrylates, polymethacrylates, polyvinylamides and the likes.

In the phase change material, a plurality of micro heating particles which generate heat by absorbing electromagnetic wave energy may be distributed. The micro heating particles have characteristics of generating heat by rapidly increasing temperature when electromagnetic wave energy is supplied by laser light, and characteristics of being distributed evenly in the wax. To have those characteristics, the micro heating particles may include a core including a metal component and a hydrophobic surface. For example, the micro heating particles may have a molecular structure including a core composed of Fe, and a plurality of surfactant that wraps around the Fe and is coupled to the Fe. The micro heating particles may be stored in a state of being distributed in carrier oil. The carrier oil may be hydrophobic so that the micro heating particles having a hydrophobic surface structure may be uniformly distributed. Carrier oil in which micro heating particles are distributed is poured to the melted phase change material and then mixed. Subsequently, the mixed material is injected into the sample distribution channel 314 and then solidified so that the sample distribution channel 314 may be blocked.

The micro heating particles are not limited to the above-mentioned polymer particle, and may be implemented as other types of micro heating particles, such as quantum dots or magnetic beads. In addition, the micro heating particles may be microscopic metal oxide, such as $Al_2O_3$, $TiO_2$, $Ta_2O_3$, $Fe_2O_3$, $Fe_3O_4$, or $HfO_2$. There is no need for the valve 313 to include the micro heating particles, and thus, the valve 313 may be formed of only phase change material without micro heating particles. At least one portion of the platform 100 may be transparent so that electromagnetic waves projected from the outside of the platform 100 may be emitted to the valve 313.

The microfluidic structures may further include a measuring chamber 50. The sample distribution channel 314 may be connected to the measuring chamber 50 which stores supernatant separated from the sample. The measuring chamber 50 may be connected to a dilution chamber 60 via a valve 51. The valve 51 may employ a microfluidic valve, which is the same shape as the above mentioned valve 313.

The microfluidic structures may further include the dilution chamber 60. The dilution chamber 60 is configured to supply a sample dilution buffer in which supernatant and dilution buffer is mixed by a certain ratio. In the dilution chamber 60, a certain amount of dilution buffer is stored in consideration of a dilution ratio of supernatant and dilution buffer required to perform a test. The measuring chamber 50 may be designed to have a capacity to store a pre-determined amount of a sample in consideration of a dilution ratio. As long as a state where the valve 51 is closed is kept, a sample exceeding the capacity of the measuring chamber 50 may not be introduced into the measuring chamber 50. Only a required amount of supernatant may be supplied to the dilution chamber 60. By precisely designing a position where the sample distribution channel 314 and the first collection unit 311 are connected, the sample distribution channel 314 and the dilution chamber 60 may be directly connected to each other without the measuring chamber 50.

The microfluidic structures may further include a plurality of reaction chambers 70. The plurality of reaction chambers 70 may be disposed in an outer side of the dilution chamber 60. The plurality of reaction chambers 70 may be connected to the dilution chamber 60 via a distribution channel 61. The distribution of the sample dilution buffer via the distribution channel 61 may be controlled by a valve 62. The valve 62 may employ a microfluidic valve, which is the same shape as the above mentioned valve 313.

In the plurality of reaction chambers 70, a reagent performing a different type of reaction with sample dilution buffer may be stored. During the manufacture of the microfluidic device, the reagent may be inserted before the first substrate and the second substrate, both of which form the platform 100, are bonded. The plurality of reaction chambers 70 may be a chamber having a vent and an inlet, instead of a closed-type chamber. In this case, the reagent may be injected into the plurality of reaction chambers 70 prior to performing the test. The reagent may be in liquid or freeze-dried solid state.

For example, during the manufacture of the microfluidic device, a liquid reagent may be injected into the plurality of reaction chambers 70 before the first substrate and the second substrate, both of which form the platform 100, are bonded, and the liquid reagent may be simultaneously freeze-dried by the lyophilization program. Subsequently, a microfluidic device including the freeze-dried reagent by the bond of the first substrate and the second substrate may be provided. In addition, a cartridge provided with the freeze-dried reagent may be injected into the plurality of reaction chambers 70. The freeze-dried reagent may be a reagent formed in a way that a filler and a surfactant are added to liquid reagent and then freeze-dried. The filler allows the freeze-dried reagent to have a porous structure so that diluent mixed with a sample is easily dissolved when inserted into the plurality of reaction chambers 70. For example, the filler may include at least one of bovine serum albumin (BSA), polyethylene glycol (PEG), dextran, mannitol, polyalcohol, myo-inositol, citric acid, ethylene diamine tetra acetic acid disodium salt (EDTA2Na) and polyoxyethylene glycol dodecyl ether (BRIJ-35). For example, the surfactant may include at least one of polyoxyethylene, lauryl ether, octoxynol, polyethylene alkyl alcohol, nonylphenol polyethylene glycol ether (ethylene oxid), ethoxylated tridecyl alcohol, polyoxyethylene nonylphenyl ether phosphate sodium salt, and sodium dodecyl sulfate.

The microfluidic structures may further include a confirmation chamber 71 to confirm whether a sample mixture is injected into all of the plurality of reaction chambers 70. Reagent is not accommodated in the confirmation chamber 71. The confirmation chamber 71 may be provided on an end portion of the distribution channel 61. The sample mixture firstly fills the plurality of chambers 70 most adjacent to the dilution chamber 60, and lastly fills the confirmation chamber 71. Therefore, when it is confirmed that the sample mixture fills the confirmation chamber 71, it may be confirmed that the sample mixture has filled the plurality of reaction chambers 70.

The microfluidic structures may further include an air vent configured to discharge air filling inside the microfluidic device.

Figure 2A:
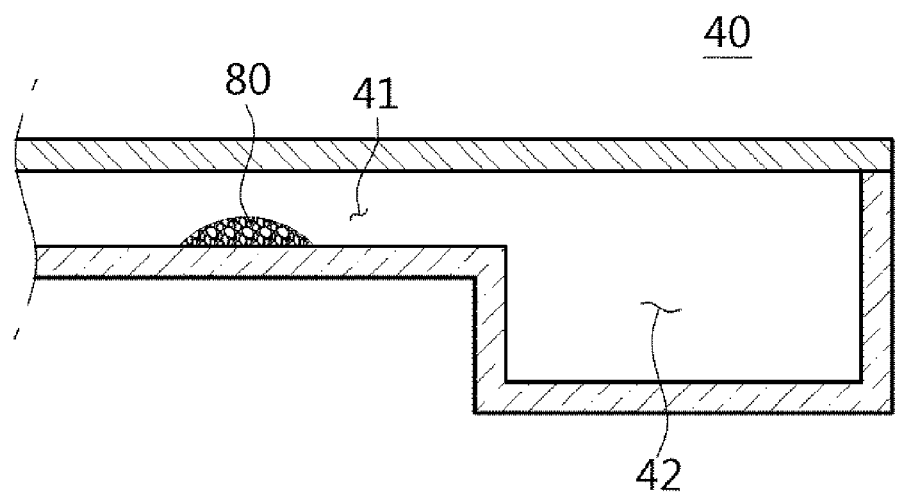
FIGS. 2A and 2B are views illustrating a position where a dye is disposed on an excess sample chamber of a microfluidic device in accordance with an exemplary embodiment.
Figure 2B:
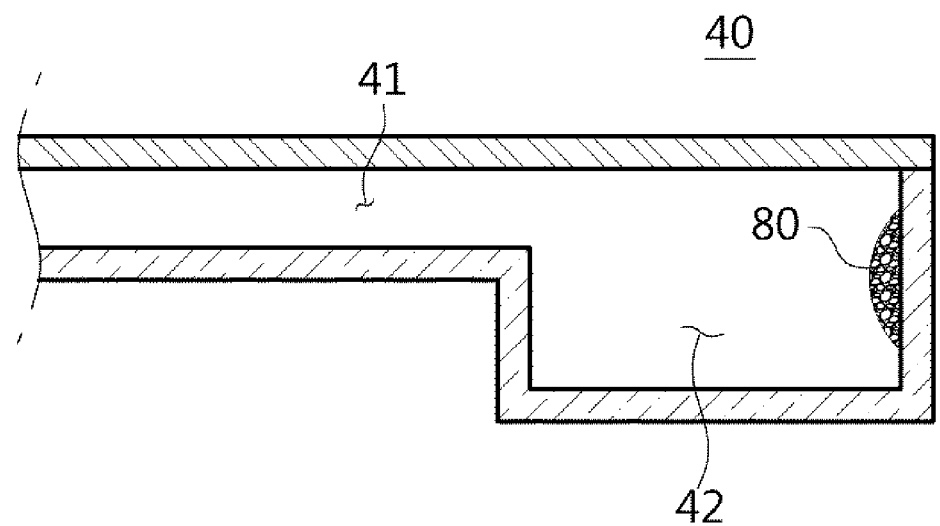

FIGS. 2A and 2B are views illustrating a position where a dye is disposed on an excess sample chamber of a microfluidic device in accordance with an exemplary embodiment. Certain reference numerals described below may be shown in FIG. 1.

The excess sample chamber 40 may include a channel 41 and an accommodation unit 42 (e.g., accommodator).

The channel 41 may be connected to at least one sample distribution chamber 31 and 32 to allow a sample accommodated in the at least one sample distribution chamber 31 and 32 to be moved. For example, the channel 41 may be connected to the second sample distribution 32 to allow a sample accommodated in the second sample distribution 32 to be moved toward the accommodation unit 42.

The accommodation unit 42 may accommodate a sample passed through the channel 41 and may be connected to the channel 41 to be disposed on an outer side of the channel 41 in the radial direction of the platform 100. That is, the accommodation unit 42 may be formed on an end portion of the channel 41 facing the outer side in the radial direction of the platform 100.

A sample introduced to the excess sample chamber 40 may be dyed by a dye 80. Particularly, the sample dyed by the dye 80 may be introduced to the excess sample chamber 40. Alternatively, at the inside of the excess sample chamber 40, a sample may be dyed by the dye 80.

As illustrated in FIGS. 2A and 2B, the dye 80 may be disposed inside the excess sample chamber 40 to dye a sample introduced to the excess sample chamber 40. The dye 80 may be applied to an inner wall of the excess sample chamber 40. Particularly, the dye 80 may be disposed in at least one of the channel 41 (FIG. 2A) or the accommodation unit 42 (FIG. 2B) of the excess sample chamber 40.

Alternatively, the dye 80 may be disposed on a flow path connecting at least one sample distribution chamber 31 and 32 to the excess sample chamber 40. Particularly, the dye 80 may be disposed on the connection channel 90 (refer to FIG. 1) connecting the second sample distribution chamber 32 to the excess sample chamber 40.

The dye 80 may play a role of reducing transparency of a sample. When the transparency of a sample is reduced, the optical density of a sample may be increased. In general, there is no substantial difference between the optical density of the excess sample chamber 40 filled with a material having high transparency and the optical density of the excess sample chamber 40 not filled with a sample. In other words, there is no substantial difference between the optical density of the excess sample chamber 40 filled with a material having high transparency and the optical density of the excess sample chamber 40 to which a sample is not introduced. Therefore, when a sample has high transparency, it may be difficult to determine whether a sample is introduced to the excess sample chamber 40 by measuring the optical density. The dye 80 may be used to relieve these difficulties. As mentioned above, the dye 80 may reduce the transparency of a sample so that whether a sample is introduced to the excess sample chamber 40 may be easily determined by measuring the optical density even though a sample has high transparency.

Figure 3:
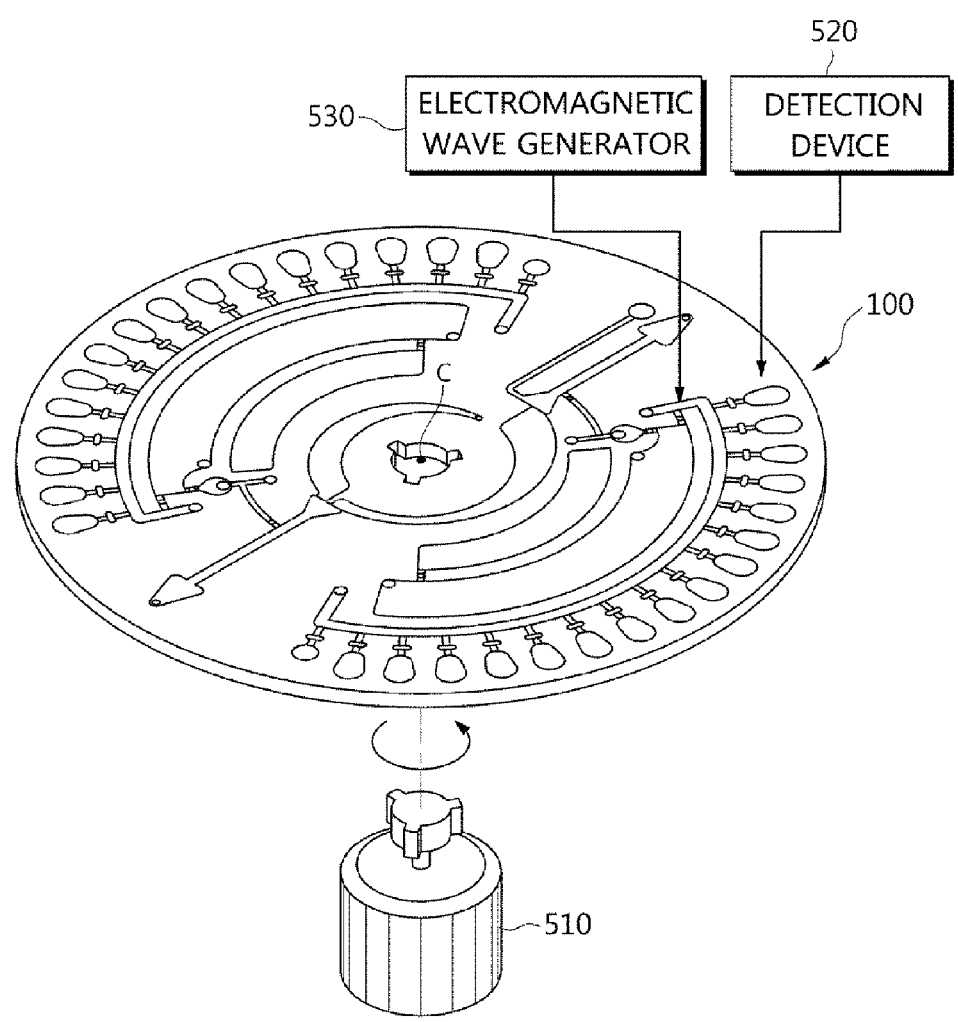
FIG. 3 is a view schematically illustrating a configuration of a detection device configured to detect a sample inserted into a microfluidic device in accordance with an exemplary embodiment.
Figure 4:
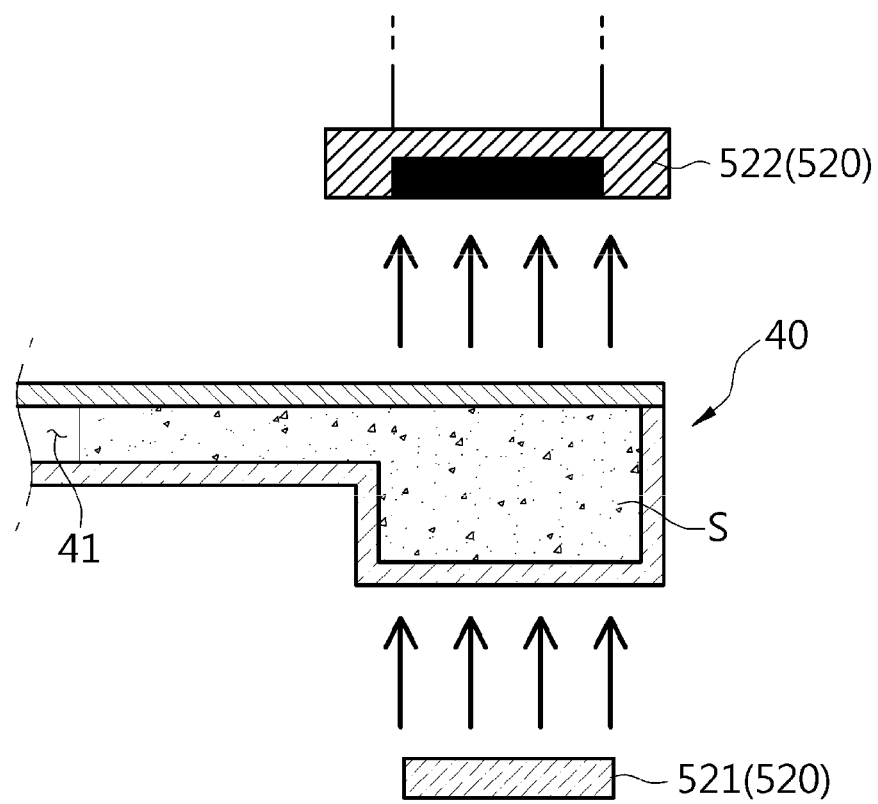
FIG. 4 is a view schematically illustrating a process of measuring an optical density of an excess sample chamber of a microfluidic device in accordance with an exemplary embodiment.

FIG. 3 is a view schematically illustrating a configuration of a detection device configured to detect a sample inserted into a microfluidic device in accordance with an exemplary embodiment and FIG. 4 is a view schematically illustrating a process of measuring an optical density of an excess sample chamber of a microfluidic device in accordance with an exemplary embodiment. Certain reference numerals described below may be shown in FIGS. 1 and 2A-2B.

As illustrated in FIGS. 3 and 4, the microfluidic device may further include a rotation driving unit 510 configured to rotate the platform 100. The rotation driving unit 510 rotates the platform 100 to move a sample to a certain position in the platform 100. In addition, the rotation driving unit 510 rotates the platform 100 to centrifuge a sample and to move the separated supernatant to a certain position in the microfluidic device. In addition, the rotation driving unit 510 stops the platform 100 at a certain position so that the plurality of reaction chambers 70 faces a detection device 520. The rotation driving unit 510 stops the platform 100 at a certain position so that the valves 51, 62, and 313 face an electromagnetic wave generator 530. The rotation driving unit 510 may include a motor drive device configured to control an angular position of the platform 100. For example, the motor drive device may include at least one a step motor and a direct current motor.

The microfluidic device may further include the detection device 520. The detection device 520 may detect an optical property, such as fluorescence, luminance, or light absorbing properties of the material to be detected. A detailed description of the detection device 520 will be described later.

The microfluidic device may further include the electromagnetic wave generator 530. The electromagnetic wave generator 530 configured to operate the valves 51, 62, and 313 may emit laser light. The electromagnetic wave generator 530 may be moved to the radial direction of the platform 100.

Hereinafter, a process of analyzing sample by using the microfluidic device will be described.

A sample is injected into the sample chamber 10. A dilution buffer in a liquid state, such as buffer solution or distilled water, is injected into the dilution chamber 60. At this time, an appropriate amount of dilution buffer is injected so that a dilution ratio of the sample dilution buffer is appropriate for the test items.

The platform 100 is mounted to the rotation driving unit 510. The rotation driving unit 510 rotates the platform 100 at a low speed. According to an exemplary embodiment, the term low speed refers to an appropriate speed to move a sample from the sample chamber 10 to the first sample distribution chamber 31 and the second distribution chamber 32. When the platform 100 is rotated, a sample accommodated in the sample chamber 10 is moved to the first sample distribution chamber 31 by the centrifugal force and fills the first sample distribution chamber 31. When the sample fills the first sample distribution chamber 31 completely, the sample is introduced into the sample conveying unit 20 via the first connection unit 21. By centrifugal force, the sample flows along the outer wall 25 of the sample conveying unit 20 and then is introduced into the second distribution chamber 32 via the second connection unit 22. All the rest of the sample, which is remaining after filling the second sample distribution chamber 32 completely, is moved to the excess sample chamber 40 along with the connection channel 90 to be accommodated.

Next, an operation for performing the sample analysis will be described.

For example, when the test items of the second analysis chamber 102 do not require centrifugation, the analysis by using the second analysis chamber 102 may be performed first. The rotation driving unit 510 rotates the platform 100 so that the valve 313 faces the electromagnetic wave generator 530. When electromagnetic waves are emitted to the valve 313, a valve material composing the valve 313 is melted by the energy and then a sample is introduced into the dilution chamber 60. The rotation driving unit 510 may perform a motion of rotating the platform 100 from side to side by several times. By this rotation, a sample dilution buffer, in which the sample and the dilution buffer are mixed, is generated. The rotation driving unit 510 rotates the platform 100 so that the valve 62 faces the electromagnetic wave generator 530. When electromagnetic waves are emitted to the valve 62, a valve material composing the valve 62 is melted by the energy and then the distribution channel 61 is opened. When the platform 100 is rotated, the sample dilution buffer may be introduced into the plurality of reaction chambers 70 and the confirmation chamber 71 via the distribution channel 61 by centrifugal force. The detection device 520 faces the confirmation chamber 71 and detects the optical density. Therefore, whether the sample dilution buffer is introduced into the confirmation chamber 71 may be confirmed. A reagant accommodated in the plurality of reaction chambers 70 is mixed with the sample dilution buffer. To mix the reagent and the sample dilution buffer, the rotation driving unit 510 may perform a motion of rotating the platform 100 from side to side by several times. The plurality of reaction chambers 70 faces the detection device 520 in order, and an optical property, such as fluorescence, luminance, or light absorbing properties of the mixture is detected by emitting light to the mixture of the reagent and the sample dilution buffer. Through those operations, it is detected whether a certain material is present in the mixture or how much of the certain material is present in the mixture.

By using the first analysis chamber 101, an operation for testing test items that require centrifugation may be performed. The rotation driving unit 510 rotates the platform 100 at high speed. According to an exemplary embodiment, the term 'high speed' may refer to the rotation speed when a sample is centrifuged. When the platform 100 is rotated, only supernatant is collected in the first collection unit 311, and a heavy mass of material is collected in the second collection unit 312. The rotation driving unit 510 rotates the platform 100 so that the valve 313 faces the electromagnetic wave generator 530. When electromagnetic waves are emitted to the valve 313, a valve material composing the valve 313 is melted by the energy and then the supernatant is introduced into the dilution chamber 60. The rotation driving unit 510 may perform a motion of rotating the platform 100 from side to side by several times to mix the supernatant and the dilution buffer. By this rotation, a sample dilution buffer, in which the supernatant and the dilution buffer are mixed, is generated. The rotation driving unit 510 rotates the platform 100 so that the valve 62 faces the electromagnetic wave generator 530. When electromagnetic waves are emitted to the valve 62, a valve material composing the valve 62 is melted by the energy and then the distribution channel 61 is opened. When the platform 100 is rotated, the sample dilution buffer is introduced into the plurality of reaction chambers 70 and the confirmation chamber 71 via the distribution channel 61 by the centrifugal force. The detection device 520 faces the confirmation chamber 71 and detects the optical density. Therefore, whether the sample dilution buffer is introduced into the confirmation chamber 71 may be confirmed. A reagant accommodated in the plurality of reaction chambers 70 is mixed with the sample dilution buffer. To mix the reagent and the sample dilution buffer, the rotation driving unit 510 may perform a motion of rotating the platform 100 from side to side by several times. The plurality of reaction chambers 70 faces the detection device 520 in order, and an optical property, such as fluorescence, luminance, or light absorbing properties of the mixture is detected by emitting light to the mixture of the reagent and the sample dilution buffer. Through those operations, it is detected whether a certain material is present in the mixture or how much of the certain material is present in the mixture.

In the above-mentioned process of sample analysis, after the sample analysis that requires centrifugation is completed, the sample analysis that does not require the centrifugation may be performed, although the sequence of analysis of a sample is not limited thereto. For example, a sample is distributed from the sample chamber 10 to the first sample chamber 31 and the second sample chamber 32 at the same time. A first sample dilution buffer is generated in a way that a sample that does not require centrifugation and a dilution buffer are mixed. A second sample dilution butter is generated in a way that a supernatant separated from a sample that requires the centrifugation by the centrifugation and a dilution buffer are mixed. The first sample dilution buffer and the second sample dilution buffer may be moved to corresponding analysis chambers 101 and 102 to be mixed with reagent and then the detection device 520 may detect the presence of a certain material in the mixture and how much of the certain material is present in the certain material.

When an amount of a sample injected into a microfluidic device is insufficient, it may be difficult to perform the centrifugation or metering and thus the wrong test results may be calculated. Therefore, whether the amount of a sample injected into the microfluidic device is sufficient may enormously influence the test results. Whether the amount of a sample injected into the microfluidic device is sufficient may be confirmed by measuring the optical density of the excess sample chamber 40. For example, the optical properties of the excess sample chamber 40 may be measured by using the detection device 520. When the optical density of the excess sample chamber 40 is higher than the reference optical density, it may be determined that a sufficient amount of a sample is injected into the microfluidic device. Conversely, when the optical density of the excess sample chamber 40 is lower than the reference optical density, it may be determined that an insufficient amount of a sample is injected into the microfluidic device. When it is determined that a sufficient amount of a sample is injected into the microfluidic device, the test may proceed. When it is determined that an insufficient amount of a sample is injected into the microfluidic device, the test may be stopped. The reason for measuring the optical properties of the excess sample chamber 40 to determine whether an appropriate amount of a sample is injected into the microfluidic device is the following. When a sufficient amount of a sample is injected into the microfluidic device, the sample may fill the first sample distribution chamber 31 and the second sample distribution chamber 32 and then reach the excess sample chamber 40. Conversely, when an insufficient amount of a sample is injected into the microfluidic device, the sample may not reach the excess sample chamber 40. In other words, a sample being present in the excess sample chamber 40 may represent that a sufficient amount of a sample is supplied to the first sample distribution chamber 31 and the second sample distribution chamber 32. Therefore, whether an appropriate amount of a sample is injected into the microfluidic device may be determined by measuring the optical density of the excess sample chamber 40.

As illustrated in FIG. 4, the detection device 520 may include a light emitting unit 521 and a light receiving unit 522 to measure the optical density of the excess sample chamber 40 to confirm whether a sample is accommodated in the excess sample chamber 40. The light emitting unit 521 may emit many different types of light and is not limited to a certain type. Similarly, the light receiving unit 522 may receive many different types of light and is not limited to a certain type. The light receiving unit 522 of the detection device 520 may include a photodiode.

The excess sample chamber 40 may be disposed between the light emitting unit 521 and the light receiving unit 522. However, the position of the excess sample chamber 40 is not limited thereto. For example, the excess sample chamber 40 may be disposed on a light transmission path where a light emitted from the light emitting unit 521 of the detection device 520 is transmitted to the light receiving unit 522.

A sample may fill at least one portion of the excess sample chamber 40. For example, a sample may fill at least one of the channel 41 and the accommodation unit 42 of the excess sample chamber 40. Alternatively, a sample may fill at least portion of the accommodation unit 42 of the excess sample chamber 40.

As illustrated in FIGS. 2A and 2B, when using a dye, it may be easy to determine the presence of a sample regardless of the transparency of the sample, based on differences in the optical density of the excess sample chamber 40. Therefore, using the dye may be effective to determine whether an appropriate amount of a sample is supplied to the microfluidic device.

The sample detection method of determining whether an amount of a sample supplied to the microfluidic device is appropriate may include injecting a sample into the sample chamber 10, moving the sample injected into the sample chamber 10 to the sample distribution chambers 31 and 32, moving the rest of the sample, which is remaining after filling the sample distribution chambers 31 and 32, to the excess sample chamber 40, and measuring the optical density of the excess sample chamber 40 by using the detection device 520.

The detection method of detecting a sample to determine whether an amount of a sample supplied to the microfluidic device is appropriate may further include dying the sample introduced to the excess sample chamber 40. The dying of the sample introduced to the excess sample chamber 40 may be performed prior to measuring the optical density of the excess sample chamber 40 by using the detection device 520.

Figure 5:
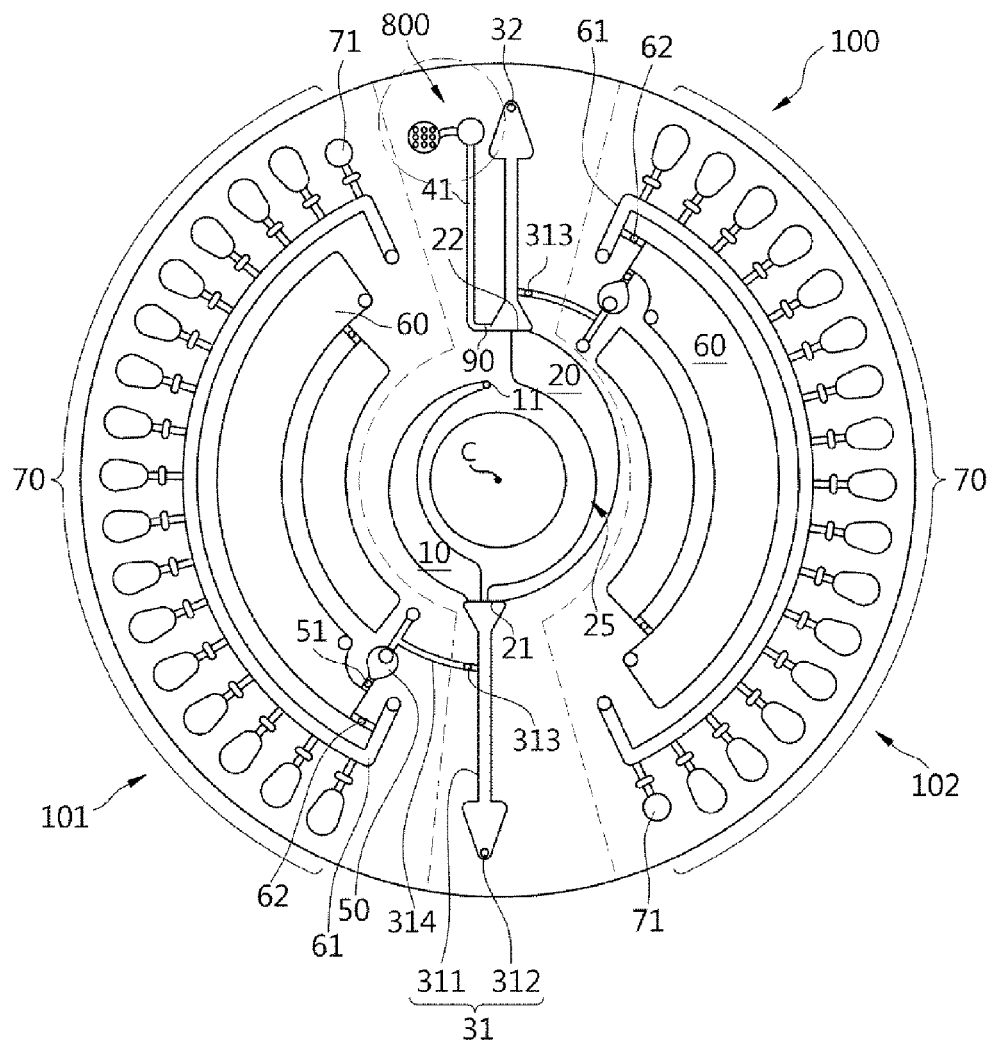
FIG. 5 is a view illustrating a microfluidic device in accordance with another exemplary embodiment.
Figure 6:
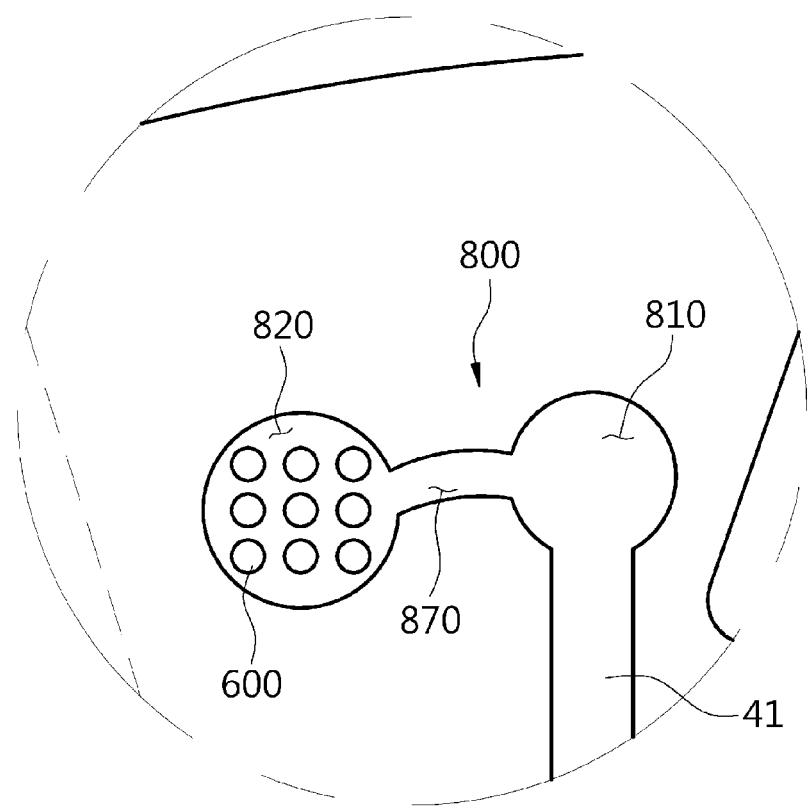
FIG. 6 is an enlarged view illustrating a first example of an excess sample chamber in accordance with another exemplary embodiment.

FIG. 5 is a view illustrating a microfluidic device in accordance with another exemplary embodiment, FIG. 6 is an enlarged view illustrating a first example of an excess sample chamber in accordance with another exemplary embodiment, and FIGS. 7A, 7B, 7C, 7D, 7E and 7F are views illustrating a variety of concave-convex structures applicable to a second excess sample chamber of a microfluidic device in accordance with another exemplary embodiment. Hereinafter, a description of the same parts as those shown in FIGS. 1 and 3 will be omitted.

As illustrated in FIGS. 5 to 7F, a structure to induce the change of the progress direction of a light, which is emitted from the light emitting unit 521 and transmitted to the light receiving unit 522, may be formed in the excess sample chamber 800. By forming the structure to induce the change of the progress direction of a light, which is emitted from the light emitting unit 521 and transmitted to the light receiving unit 522, the differences of the optical density of the excess sample chamber 800 may be clear depending on the presence of a sample regardless of the transparency of the sample. Particularly, when a sample is not supplied to the excess sample chamber 800, in the structure to induce the change of the progress direction of a light, the reflection or refraction of light may be generated and thus the optical density of the excess sample chamber 800 may be measured to be higher than the reference optical density. Conversely, when a sample is supplied to the excess sample chamber 800, in the structure to induce the change of the progress direction of a light, less reflection or less refraction of light may be generated by a matching (or substantially similar) refractive index and thus the optical density of the excess sample chamber 800 may be measured to be less than the reference optical density.

A concave-convex structure 600 may be formed in the excess sample chamber 800. In the excess sample chamber 800, the concave-convex structure 600 may be formed as an example of a structure to induce the change of the progress direction of a light, which is emitted from the light emitting unit 521 and moved to the light receiving unit 522.

The concave-convex structure 600 may be formed on at least one inner wall of the excess sample chamber 800.

The excess sample chamber 800 may include a first surface 831 and a second surface 841. The first surface 831 may be opposite to a surface 832 facing the light emitting unit 521 of the detection device 520. The second surface 841 may be opposite to a surface 842 facing the light receiving unit 522 of the detection device 520. The concave-convex structure 600 may be formed on at least one of the first surface 831 and the second surface 841 of the excess sample chamber 800.

The excess sample chamber 800 may include a first plate 850 and a second plate 860. The first plate 850 faces the light emitting unit 521. The second plate 860 faces the light receiving unit 522. The first plate 850 may represent any one of the first substrate and the second substrate of the platform 100 corresponding to the excess sample chamber 800. The second plate 860 may represent the other of the first substrate and the second substrate of the platform 100 corresponding to the excess sample chamber 800. That is, according to an exemplary embodiment, the first substrate and the second substrate may be used to refer to the first plate 850 and the second plate 860. Hereinafter, for convenience of description, the first plate 850 represents a first substrate of the platform 100 corresponding to the excess sample chamber 800 and the second plate 860 represents a second substrate of the platform 100 corresponding to the excess sample chamber 800. The concave-convex structure 600 may be formed on at least one of the first plate 850 and the second plate 860. Particularly, the concave-convex structure 600 may be formed on at least one of the inner wall of the first plate 850 and the inner wall of the second plate 860 toward the excess sample chamber 800.

The concave-convex structure 600 may be formed by corroding the inner wall of the excess sample chamber 800. To corrode the inner wall of the excess sample chamber 800, at least one of a chemical process and a physical process may be performed.

The excess sample chamber 800 may include a plurality of chambers 810 and 820. Particularly, the excess sample chamber 800 may include a first chamber 810 and a second chamber 820. The concave-convex structure 600 may be formed on at least one inner wall of the second chamber 820. In other words, the accommodation unit of the excess sample chamber 800 may include the first chamber 810 and the second chamber 820. The first chamber 810 may be disposed between the second chamber 820 and the channel 41 of the excess sample chamber 800. The channel 41 of the excess sample chamber 800 may be connected to the first chamber 810. In addition, the channel 41 of the excess sample chamber 800 may be connected to the second chamber 820. When the channel 41 of the excess sample chamber 800 is connected to the first chamber 810, a sample passed through the channel 41 may be introduced into the second chamber 820 via the first chamber 810, and when the channel 41 of the excess sample chamber 800 is connected to the second chamber 820, a sample passed through the channel 41 may be introduced into the first chamber 810 via the second chamber 820. In addition, the channel 41 of the excess sample chamber 800 may be connected to both of the first chamber 810 and the second chamber 820. When the channel 41 of the excess sample chamber 800 is connected to the first chamber 810 and the second chamber 820, a sample passed through the channel 41 may be introduced into the first chamber 810 and the second chamber 820 at the same time. Accordingly, the channel 41 of the excess sample chamber 800 may connect at least one of the first chamber 810 and the second chamber 820 to the distribution chambers 31 and 32 so that a sample accommodated in at least one of sample distribution chambers 31 and 32 may be moved.

The first chamber 810 and the second chamber 820 may be connected to each other so that a sample may be moved between the first chamber 810 and the second chamber 820.

The excess sample chamber 800 may further include a connection pipe 870. The connection pipe 870 may be disposed between the first chamber 810 and the second chamber 820. The connection pipe 870 may connect the first chamber 810 to the second chamber 820 so that a sample may be moved between the first chamber 810 and the second chamber 820. A width of the connection pipe 870 may be less than a width of the first chamber 810 and the second chamber 820 in the radial direction of the platform 100.

The concave-convex structure 600 may be formed in a variety of shapes.

Figure 7A:
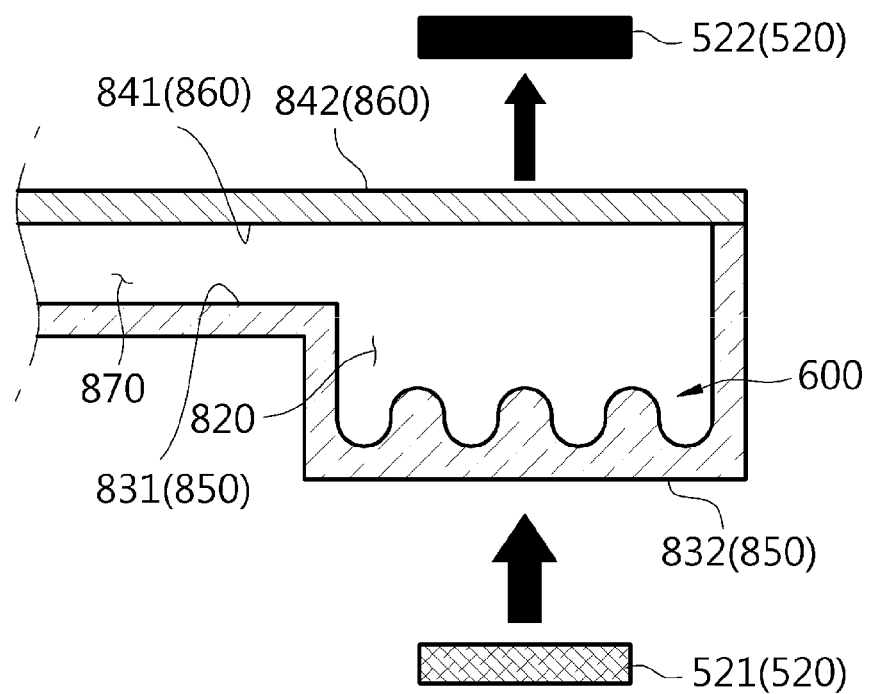
FIGS. 7A, 7B, 7C, 7D, 7E and 7F are views illustrating a variety of concave-convex structures applicable to a second excess sample chamber of a microfluidic device in accordance with another exemplary embodiment.
Figure 7B:
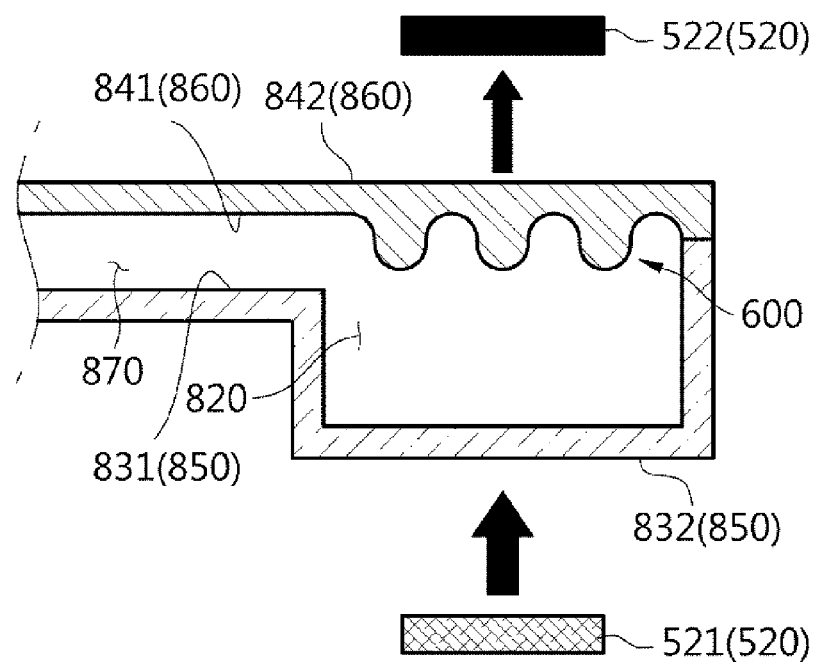
Figure 7C:
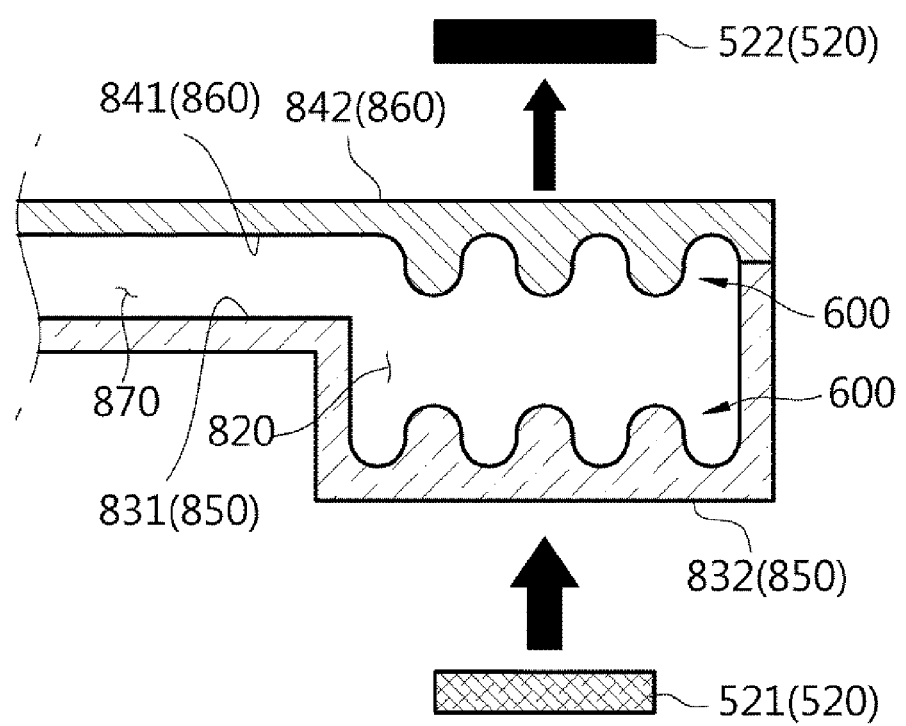

As illustrated in FIGS. 7A to 7C, the concave-convex structure 600 may have a curved surface.

Figure 7D:
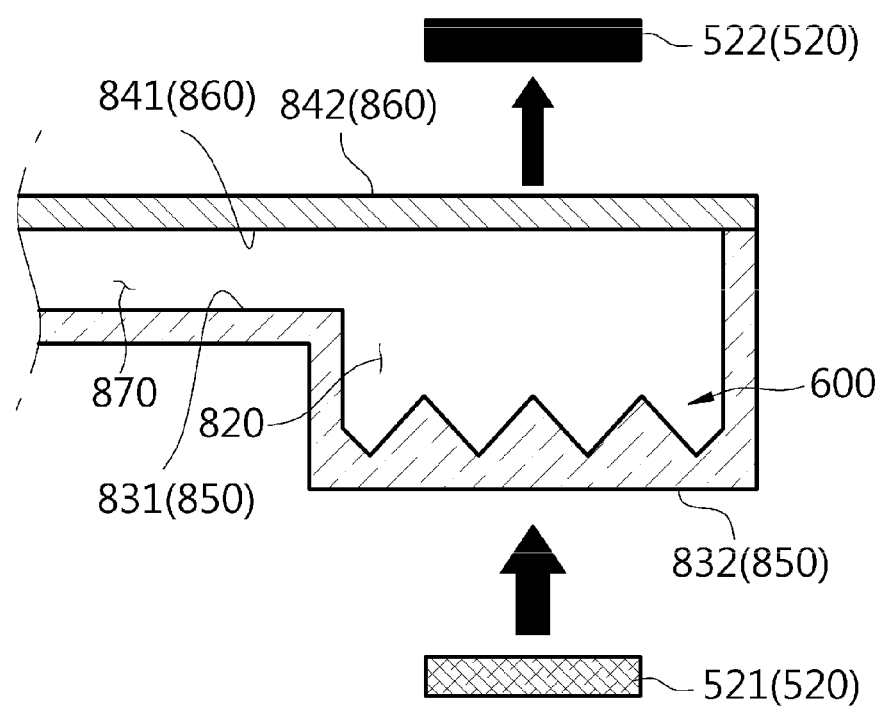
Figure 7E:
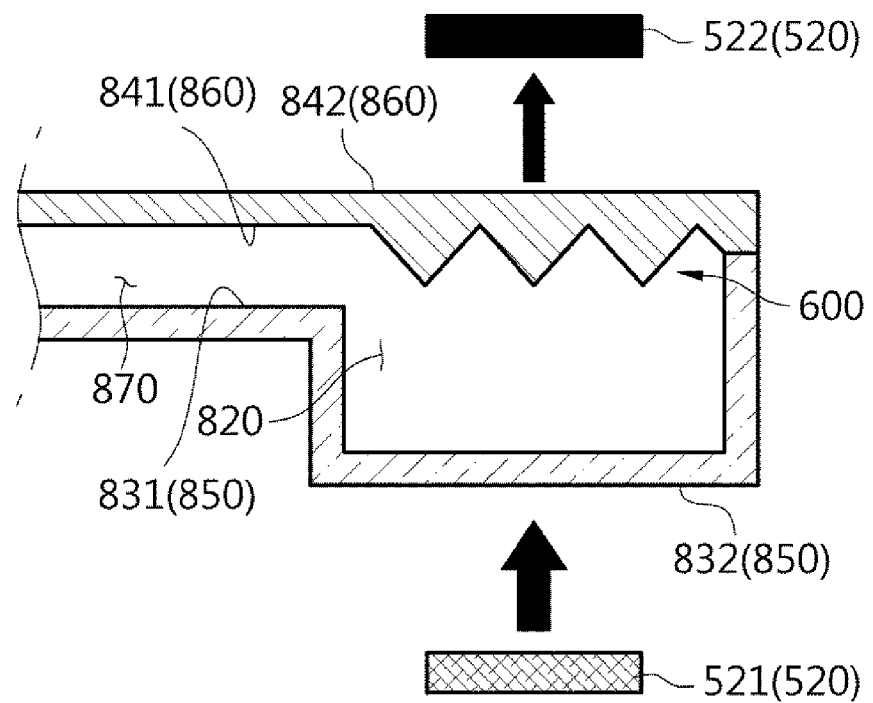
Figure 7F:
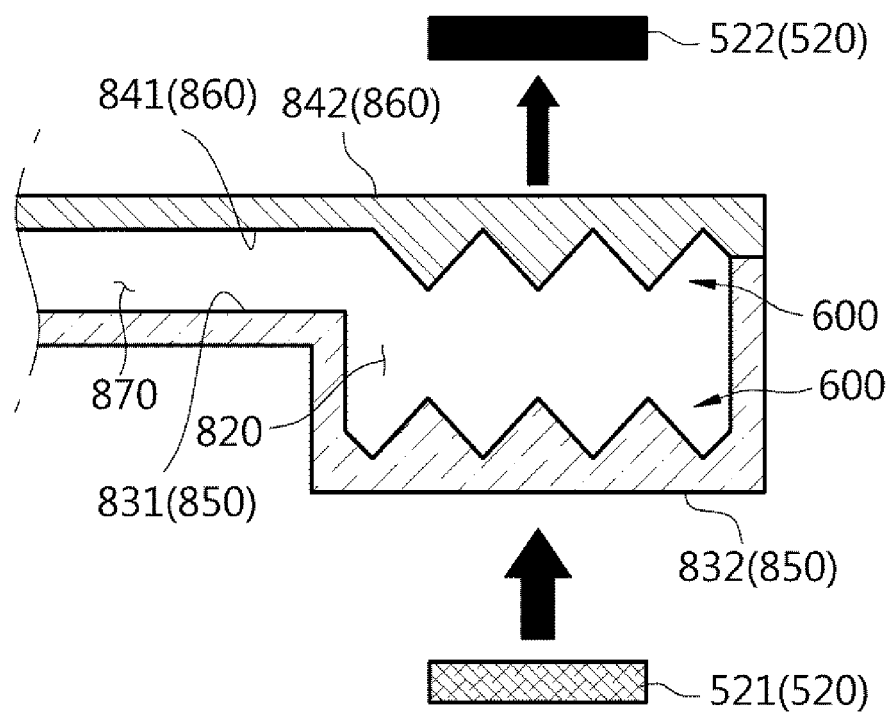

As illustrated in FIGS. 7D to 7F, the concave-convex structure 600 may have a cutting edge. In addition, the concave-convex structure 600 may have a triangular cross-section. However, the cross-section of the concave-convex structure 600 is not limited to a triangle, and thus may have a polygonal shape, such as a rectangular shape or a pentagonal shape.

Figure 8:
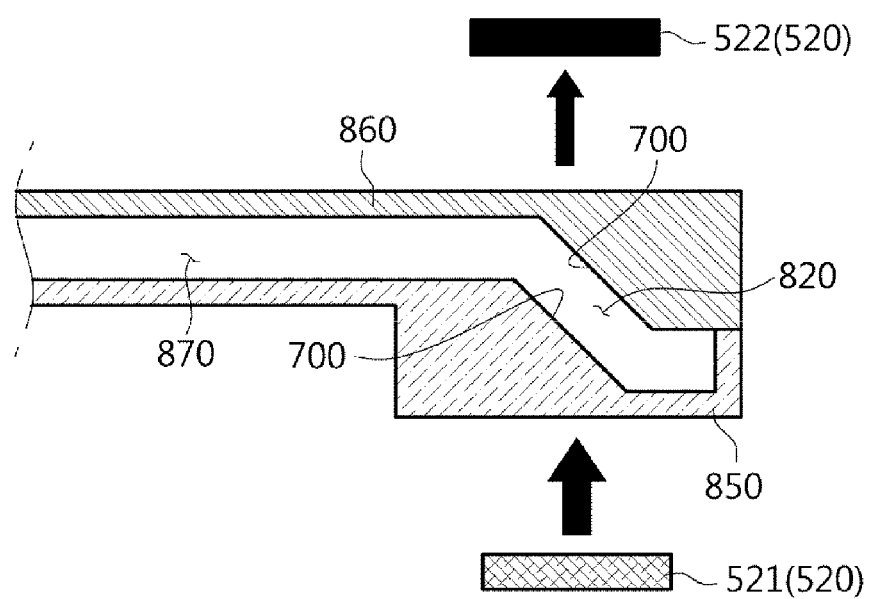
FIG. 8 is a view illustrating an inclined structure applicable to a second excess sample chamber of a microfluidic device in accordance with another exemplary embodiment.

FIG. 8 is a view illustrating an inclined structure applicable to a second excess sample chamber of a microfluidic device in accordance with another exemplary embodiment. Hereinafter, a description of the same parts as those shown in FIGS. 1 and 3 will be omitted. As illustrated in FIG. 8, a structure to induce the change of the progress direction of a light, which is emitted from the light emitting unit 521 and transmitted to the light receiving unit 522, may be formed in the excess sample chamber 800. By forming the structure to induce the change of the progress direction of light, which is emitted from the light emitting unit 521 and transmitted to the light receiving unit 522, the differences of the optical density of the excess sample chamber 800 may be clear depending on the presence of a sample. Particularly, when a sample is not supplied to the excess sample chamber 800, in the structure to induce the change of the progress direction of a light, the reflection or refraction of light may be generated and thus the optical density of the excess sample chamber 800 may be measured to be higher than the reference optical density. Conversely, when a sample is supplied to the excess sample chamber 800, in the structure to induce the change of the progress direction of a light, less reflection or less refraction of light may be generated by a matching refractive index and thus the optical density of the excess sample chamber 800 may be measured to be less than the reference optical density.

An inclined structure may be formed in the excess sample chamber 800. The inclined structure may be formed as another example of a structure to induce the change of the progress direction of a light, which is emitted from the light emitting unit 521 and moved to the light receiving unit 522.

The excess sample chamber 800 may include an inclined surface 700 inclined to the progress direction of light emitted from the light emitting unit 521 of the detection device 520 and transmitted to the light receiving unit 522. Particularly, the excess sample chamber 800 may include an inclined surface 700 inclined to the progress direction of light to totally reflect the light emitted from the light emitting unit 521 of the detection device 520. For example, the inclined surface 700 of the excess sample chamber 800 may be formed to be inclined at about 45° to the progress direction of the light. However, an inclined angle of the inclined surface 700 of the excess sample chamber 800 to the progress direction of the light may be many different angles which are appropriate to reflect a light emitted from the light emitting unit 521 of the detection device 520, and thus is not limited to being 45°.

The excess sample chamber 800 may include a plurality of chambers 810 and 820. Particularly, the excess sample chamber 800 may include a first chamber 810 and a second chamber 820. The inclined structure 700 may, for example, be formed in the second chamber 820. In other words, the accommodation unit of the excess sample chamber 800 may include the first chamber 810 and the second chamber 820. The channel 41 of the excess sample chamber 800 may connect at least one of the first chamber 810 and the second chamber 820 to at least one of the distribution chambers 31 and 32 so that a sample accommodated in at least one of sample distribution chambers 31 and 32 may be moved.

The first chamber 810 and the second chamber 820 may be connected to each other so that a sample may be moved between the first chamber 810 and the second chamber 820.

The excess sample chamber 800 may further include a connection pipe 870 (refer to FIG. 6). The connection pipe 870 may be disposed between the first chamber 810 and the second chamber 820. The connection pipe 870 may connect the first chamber 810 to the second chamber 820 so that a sample may be moved between the first chamber 810 and the second chamber 820. A width of the connection pipe 870 may be less than a width of the first chamber 810 and the second chamber 820 in the radial direction of the platform 100.

The inclined surface 700 may be formed in at least one of the first plate 850 and the second plate 860 (refer to the description of FIGS. 7A to 7F). That is, the inclined surface 700 may be formed in at least one of the inner walls of the excess sample chamber 800.

Figure 9:
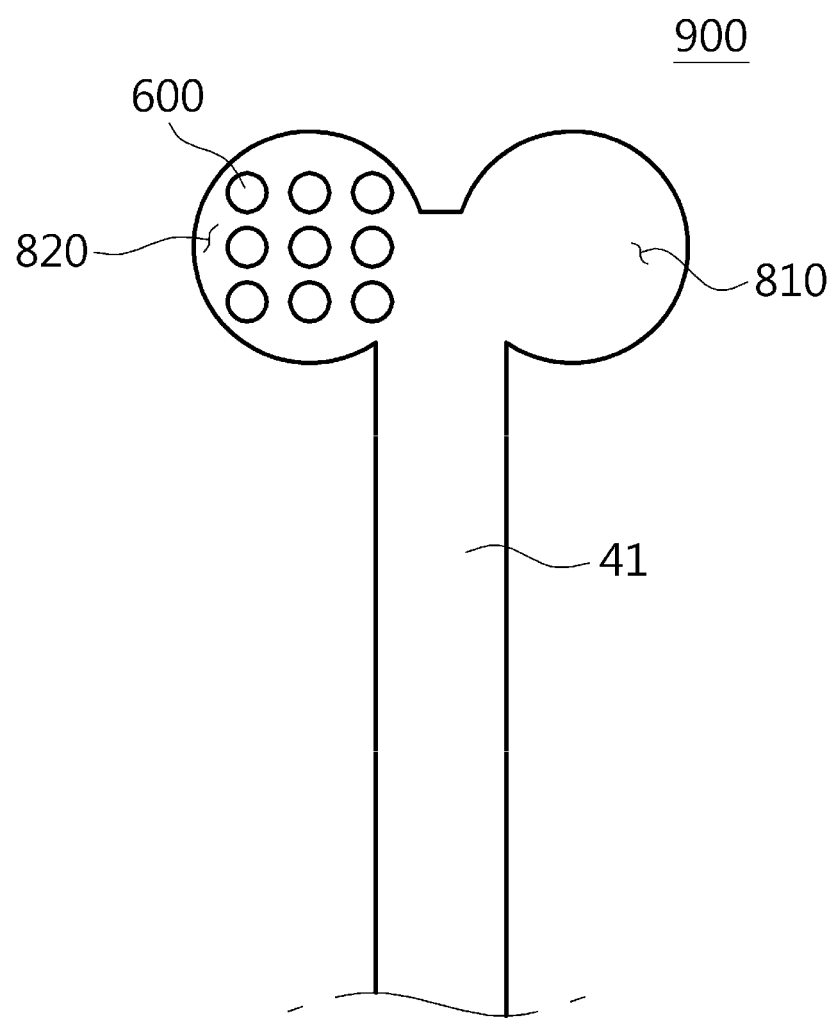
FIG. 9 is a view illustrating a second example of an excess sample chamber in accordance with another exemplary embodiment.

FIG. 9 is a view illustrating a second example of an excess sample chamber in accordance with another exemplary embodiment. Hereinafter, a description of the same parts as those shown in FIGS. 1 and 3, 5 to 8 will be omitted. As illustrated in FIG. 9, a channel 41 of the excess sample chamber 900 may connect at least one of sample distribution chambers 31 and 32 to a plurality of chambers 810 and 820 so that a sample accommodated in the at least one of sample distribution chambers 31 and 32 may be moved. Therefore, the sample passed through the channel 41 of the excess sample chamber 900 may be introduced into the first chamber 810 and the second chamber 820 at the same time. In the excess sample chamber 900, the above-mentioned concave-convex structure 600 or the inclined structure may be applied.

Figure 10:
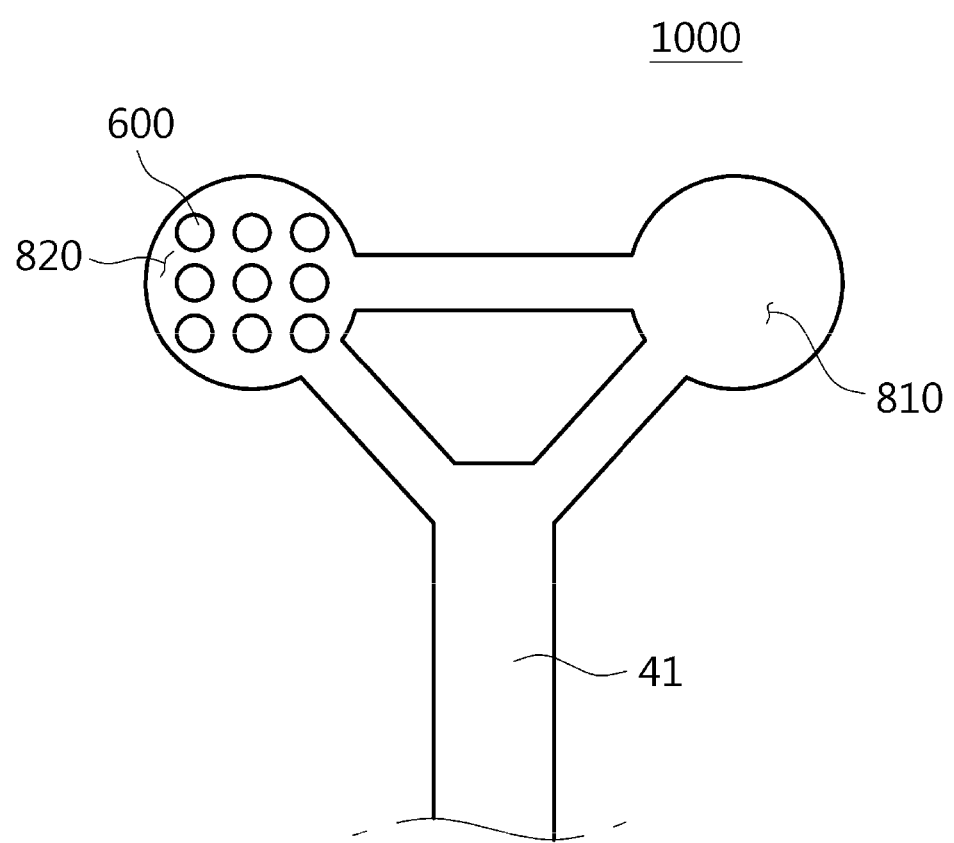
FIG. 10 is a view illustrating a third example of an excess sample chamber in accordance with another exemplary embodiment.

FIG. 10 is a view illustrating a third example of an excess sample chamber in accordance with another exemplary embodiment. Hereinafter, a description of the same parts as those shown in FIGS. 1 and 3, 5 to 8 will be omitted. An excess sample chamber 1000 may be used to mean a chamber.

As illustrated in FIG. 10, a channel 41 of the excess sample chamber 1000 may be divided to connect a first chamber 810 to a second chamber 820.

The channel 41 of the excess sample chamber 1000 may be divided to connect at least one of sample distribution chambers 31 and 32 to a plurality of chambers 810 and 820. Particularly, one end portion of the channel 41 of the excess sample chamber 1000 may be connected to the at least one of sample distribution chambers 31 and 32, and the other end portion of the channel 41 of the excess sample chamber 1000 may be divided to be connected to the first chamber 810 and the second chamber 820, respectively. Therefore, a sample passed through the channel 41 of the excess sample chamber 1000 may be introduced into the first chamber 810 and the second chamber 820 at the same time. In the excess sample chamber 1000, the above-mentioned concave-convex structure 600 or the inclined structure may be applied.

Figure 11:
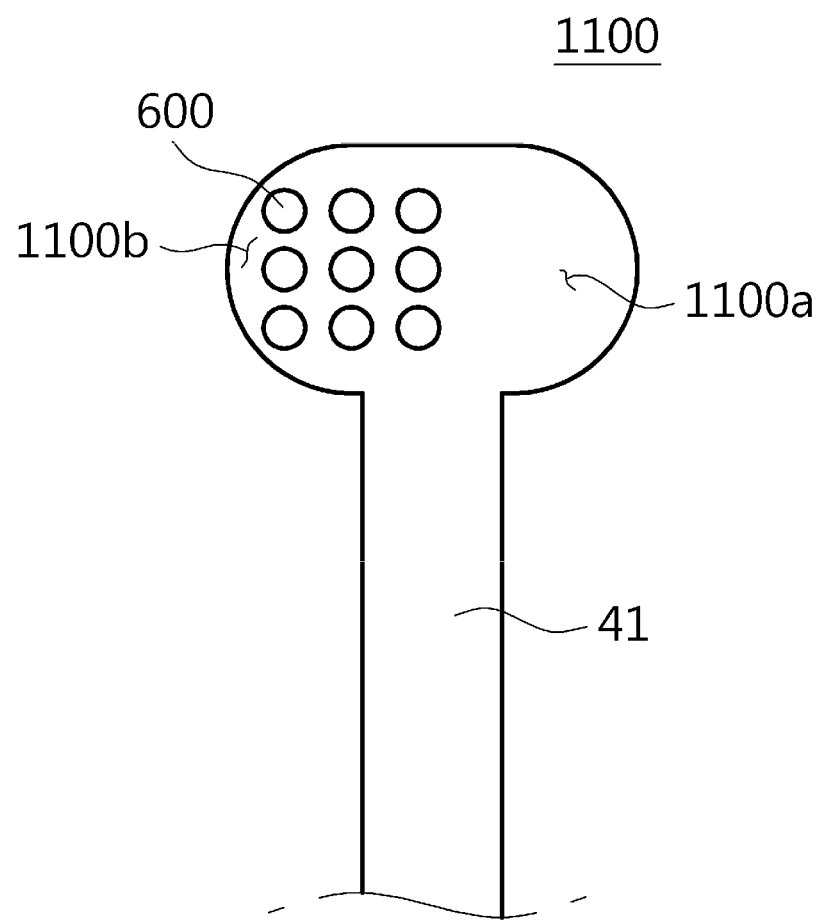
FIG. 11 is a view illustrating a fourth example of an excess sample chamber in accordance with another exemplary embodiment.

FIG. 11 is a view illustrating a fourth example of an excess sample chamber in accordance with another exemplary embodiment. Hereinafter, a description of the same parts as those shown in FIGS. 1 and 3, 5 to 8 will be omitted. As illustrated in FIG. 11, the excess sample chamber 1100 may be configured with a single chamber. In other words, an accommodation unit of the excess sample chamber 1100 may be configured with a single chamber.

On at least one inner wall of the excess sample chamber 1100, at least one of the concave-convex structure 600 and the inclined structure may be applied.

The excess sample chamber 1100 may include a first portion 1100a and a second portion 1100b. On at least one inner wall of the second portion 1100b, at least one of the concave-convex structure 600 and the inclined structure may be applied.

A channel 41 of the excess sample chamber 110 may be connected to the accommodation unit 42 so that a sample passed through the channel 41 may be introduced into the first portion 1100a and the second portion 1100b at the same time.

Hereinafter, a method of detecting a sample to determine whether an amount of a sample supplied to the microfluidic device is appropriate according to an exemplary embodiment is described. A first area may refer to an area including the first chamber 810 and the first portion 1100a. A second area may refer to an area including the second chamber 820 and the second portion 1100b. In the microfluidic device, the excess sample chamber 800 according to the first example of another exemplary embodiment, the excess sample chamber 900 according to the second example of another exemplary embodiment, the excess sample chamber 1000 according to the third example of another exemplary embodiment, or the excess sample chamber 1100 according to the fourth example of another exemplary embodiment may be applied.

The method of detecting a sample to determine whether an amount of a sample supplied to the microfluidic device is appropriate may include injecting a sample into the sample chamber 10, moving the sample injected into the sample chamber 10 to at least one of the sample distribution chambers 31 and 32, moving the rest of the sample, which is remaining after filling at least one of the sample distribution chambers 31 and 32, to the excess sample chamber 800, 900, 1000, or 1100 including the first area and the second area, measuring the optical density of the first area and the second area by using the detection device 520, and determining that an appropriate amount of a sample is supplied to the microfluidic device when the optical density of the first area is higher than the reference optical density or when the optical density of the second area is lower than the reference optical density.

When the excess sample chamber 800, 900, 1000, or 1100 includes the first area and the second area on which the concave-convex structure 600 or the inclined structure is formed, the differences of the optical density in the excess sample chamber 800, 900, 1000, or 1100 may be clear depending on the presence of a sample regardless of the transparency of the sample. Particularly, when a sample has a low transparency, e.g., whole blood, and is introduced into the excess sample chamber 800, 900, 1000, or 1100, the optical density of the first area is higher than the reference optical density (condition 1). When a sample has a high transparency, e.g., serum or plasma, is introduced into the excess sample chamber 800, 900, 1000, or 1100, the optical density of the second area is lower than the reference optical density (condition 2). When a sample has a middle level of transparency and is introduced into the excess sample chamber 800, 900, 1000, or 1100, the optical density of the first area and the second area satisfies the reference optical density, respectively (condition 3). Accordingly, when any one of condition 1, condition 2, or condition 3 is satisfied by measuring the optical density of the first area and the second area of the excess sample chamber 800, 900, 1000, or 1100, it may be determined whether a sample is introduced to the excess sample chamber 800, 900, 1000, and 1100. That is, it may be determined whether a sufficient amount of a sample is injected into the microfluidic device.

Figure 12:
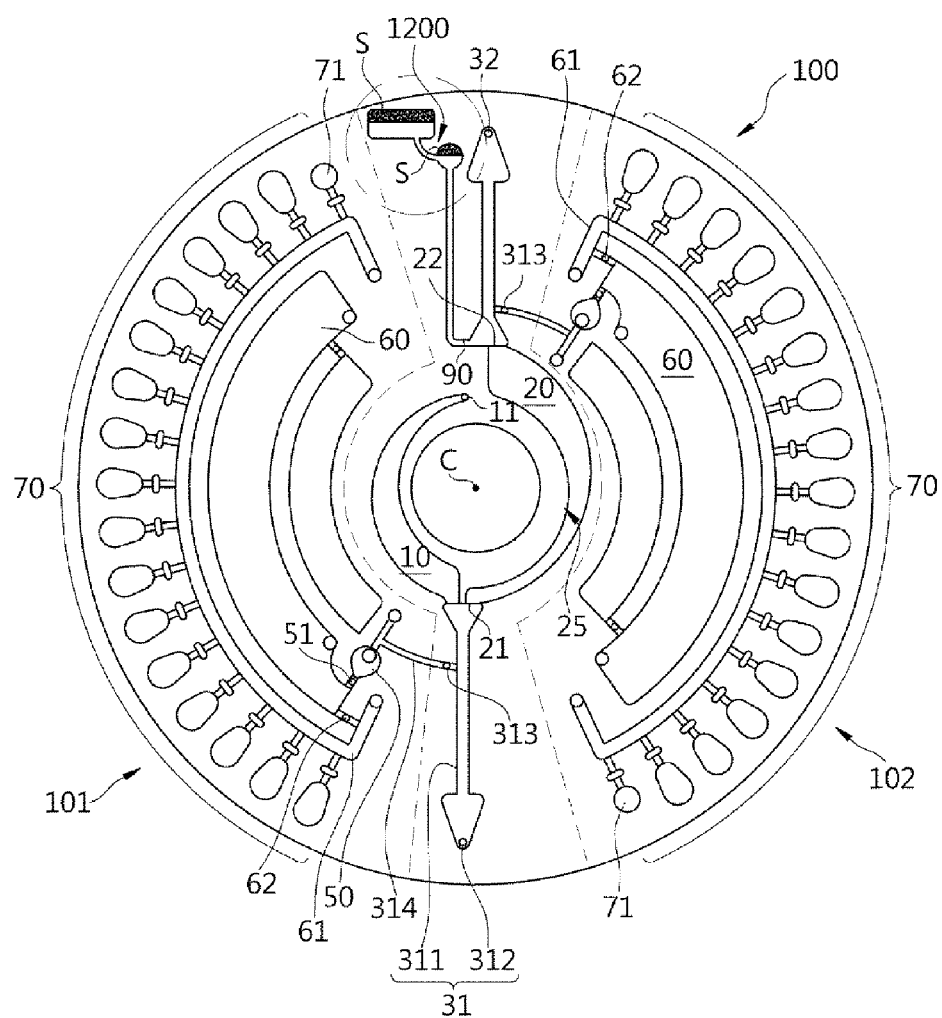
FIG. 12 is a view illustrating a microfluidic device in accordance with another exemplary embodiment.
Figure 13:
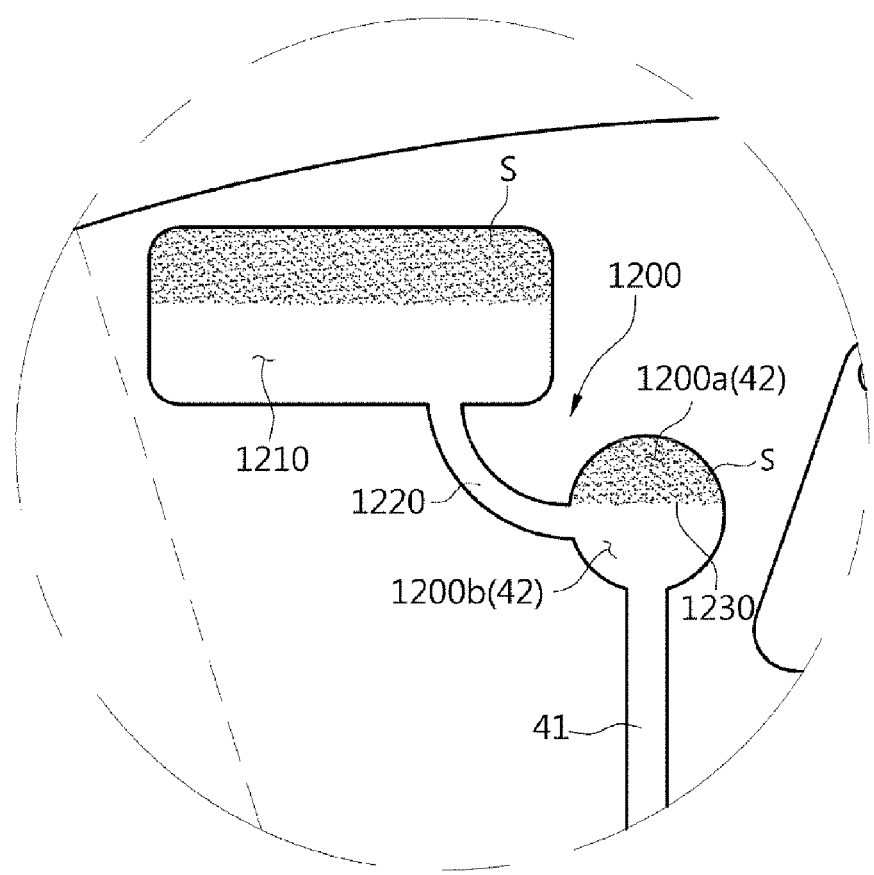
FIG. 13 is an enlarged view illustrating a portion of a microfluidic device in accordance with another exemplary embodiment.

FIG. 12 is a view illustrating a microfluidic device in accordance with another exemplary embodiment and FIG. 13 is an enlarged view illustrating a portion of a microfluidic device in accordance with another exemplary embodiment. Hereinafter, a description of the same parts as those shown in FIGS. 1 and 3 will be omitted. As illustrated in FIGS. 12 and 13, a sample may fill a part of the excess sample chamber 1200. Particularly, the sample may fill a part of an accommodation unit 42 of the excess sample chamber 1200. When the sample fills a part of the excess sample chamber 1200, the rest of the excess sample chamber 1200 may be filled with air. In other words, when a part of the excess sample chamber 1200 is filled with the sample and the rest of the excess sample chamber 1200 is filled with air, a boundary surface 1230 between the sample and air may be formed in the excess sample chamber 1200.

The microfluidic device may further include a sample accommodating chamber 1210. The sample accommodating chamber 1210 is disposed on an outer side of the excess sample chamber 1200 in a radial direction of the platform 100 and connected to the excess sample chamber 1200.

The microfluidic device may further include a sample moving channel 1220 connecting the excess sample chamber 1200 to the sample accommodating chamber 1210. A sample introduced into the excess sample chamber 1200 may be delivered to the sample accommodating chamber 1210 via the sample moving channel 1220 by the centrifugal force generated by the rotation of the platform 100. The sample moving channel 1220 may connect the accommodation unit 42 to the sample accommodating chamber 1210 so that a portion of the sample accommodated in the accommodation unit 42 is moved to the sample accommodating chamber 1210.

The accommodation unit 42 may include a first accommodation unit 1200a and a second accommodation unit 1200b. The first accommodation unit 1200a may be disposed on an outer side of the sample moving channel 1220 in the radial direction of the platform 100. The second accommodation unit 1200b may be disposed on an inner side of the sample moving channel 1220 in the radial direction of the platform 100. In addition, the second accommodation unit 1200b may face the channel 41. In other words, the second accommodation unit 1200b may be connected to the channel 41. The first accommodation unit 1200a may be filled with a sample S, and the second accommodation unit 1200b may be filled with air.

The boundary surface 1230 between a sample S accommodated in the excess sample chamber 1200 and air may be disposed on a light path (e.g., light transmission path) along which a light emitted from the light emitting unit 521 of the detection device 520 is transmitted to the light receiving unit 522 of the detection device 520. As mentioned above, when the boundary surface 1230 between a sample accommodated in the excess sample chamber 1200 and air is disposed on a light path, the differences of the optical density of the excess sample chamber 1200 may be clear depending on the presence of a sample regardless of the transparency of the sample. Particularly, a light emitted from the light emitting unit 521 may be reflected or refracted on the boundary surface 1230 and not be received by the light receiving unit 522. Accordingly, by measuring the optical density, a case where a sample having high transparency is injected into the excess sample chamber 1200 may be distinguished from a case where a sample is not injected into the excess sample chamber 1200.

Figure 14:
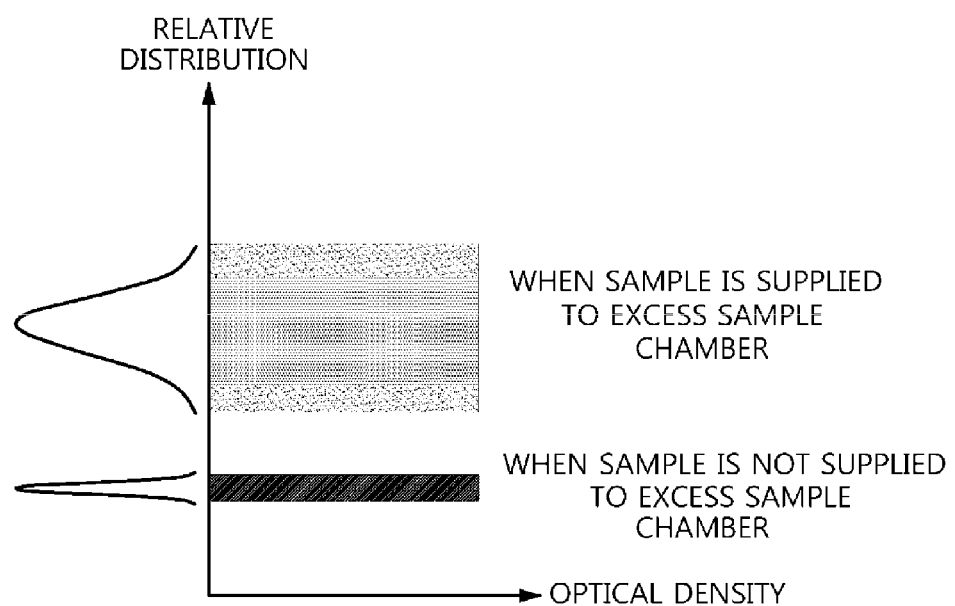
FIG. 14 is a view illustrating a distribution of the optical density depending on the presence of a first sample in an excess sample chamber of a microfluidic device in accordance with another exemplary embodiment.

FIG. 14 is a view illustrating a distribution of the optical density depending on the presence of a first sample of an excess sample chamber of a microfluidic device in accordance with another exemplary embodiment. Hereinafter, a description of the same parts as those shown in FIGS. 1 and 3 will be omitted. Certain reference numerals described below may be shown in FIGS. 12 and 13.

As illustrated in FIG. 14, when the boundary surface 1230 is disposed on the light path, the differences of the optical density may be clear depending on the presence of a sample. A sample may be formed in a way that a fluid and a material in a shape of particles having a higher density than the fluid are mixed. For example, a sample may include a biological sample, such as blood, saliva, and urine. A first sample may be whole blood. The optical density of the excess sample chamber 1200 to which the first sample is introduced may be larger than the optical density of the excess sample chamber 1200 to which a sample is not introduced.

Figure 15:
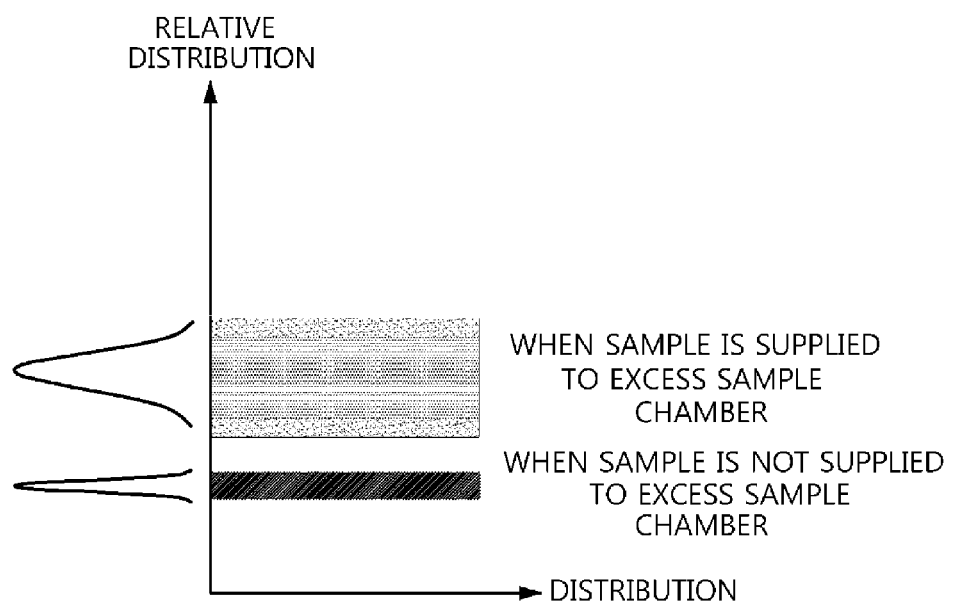
FIG. 15 is a view illustrating a distribution of the optical density depending on the presence of a second sample in an excess sample chamber of a microfluidic device in accordance with another exemplary embodiment.

FIG. 15 is a view illustrating a distribution of the optical density depending on the presence of a second sample of an excess sample chamber of a microfluidic device in accordance with another exemplary embodiment. Hereinafter, a description of the same parts as those shown in FIGS. 1 and 3, 5 to 8 will be omitted. Certain reference numerals described below may be shown in FIGS. 12 and 13.

As illustrated in FIG. 15, when the boundary surface 1230 is disposed on the light path, the differences of the optical density may be clear depending on the presence of a sample. A sample may be formed in a way that a fluid and a material in a shape of particles having a higher density than the fluid are mixed. For example, a sample may include a biological sample, such as blood, saliva, and urine. A second sample may be serum or plasma having higher transparency than whole blood. The optical density of the excess sample chamber 1200 to which the second sample is introduced may be larger than the optical density of the excess sample chamber 1200 to which any sample is not introduced. Although the differences of the optical density depending on the presence of the second sample is not larger than the differences of the optical density depending on the presence of the first sample, an overlap between the distributions of the optical density depending on the presence of the second sample is not generated, and thus, the differences of the optical density may be clear depending on the presence of the second sample.

FIGS. 16A to 16D are views illustrating the shape of a boundary surface between a sample and air according to characteristics of the surface of excess sample chamber in accordance with another exemplary embodiment. Hereinafter, a description of the same parts as those shown in FIGS. 1 and 3, 5 to 8 will be omitted. Certain reference numerals described below may be shown in FIGS. 12 and 13.

As illustrated in FIGS. 16A to 16D, the inner surface of the excess sample chamber 1200 may be treated by at least one of a hydrophilic treatment to form a hydrophilic material, and a hydrophobic treatment to form a hydrophobic material. Particularly, the first plate 850 (refer to the description of FIGS. 7A to 7F) and the second plate 860 (refer to the description of FIGS. 7A to 7F) may be treated by at least one of a hydrophilic treatment and a hydrophobic treatment. In other words, the first surface 831 (refer to the description of FIGS. 7A to 7F) and the second surface 841 (refer to the description of FIGS. 7A to 7F) may be treated by at least one of a hydrophilic treatment and a hydrophobic treatment. As mentioned above, when the inner surface of the excess sample chamber 1200 is treated by at least one of a hydrophilic treatment and a hydrophobic treatment, the discrimination of the optical density of the excess sample chamber 1200 depending on the presence of the sample may be improved by increasing an amount of light reflected or refracted on the boundary surface 1230 of the sample and air.

Figure 16A:
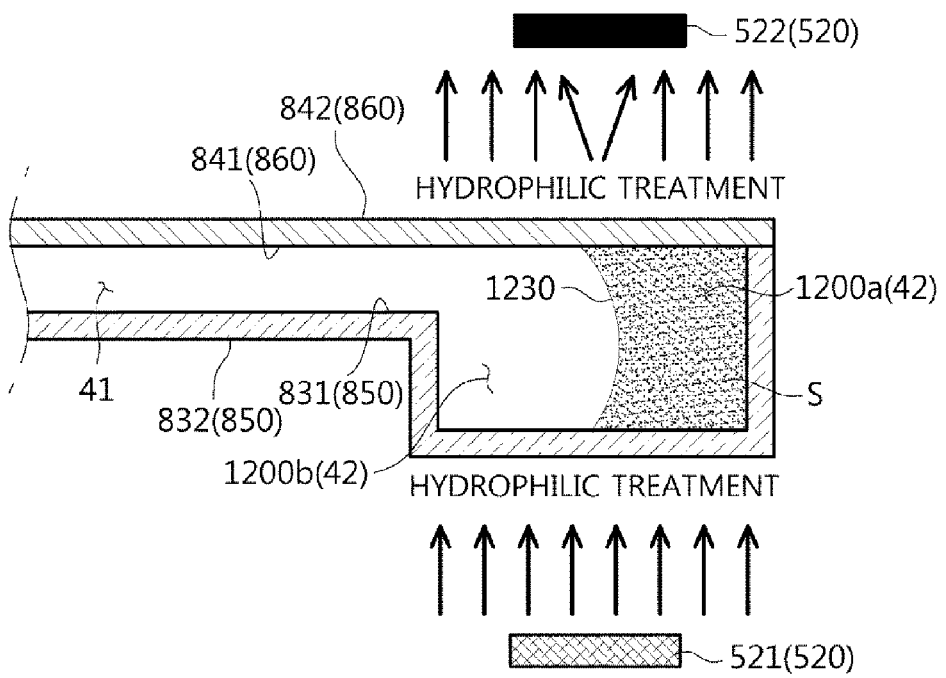
FIGS. 16A, 16B, 16C and 16D are views illustrating the shape of a boundary surface between a sample and air according to characteristics of the surface of an excess sample chamber in accordance with another exemplary embodiment.

As illustrated in FIG. 16A, when all of the first surface 831 of the first plate 850 and the second surface 841 of the second plate 860 forming the excess sample chamber 1200 are treated by a hydrophilic treatment, a boundary surface 1230 may be formed in a concave shape with respect to a sample.

Figure 16B:
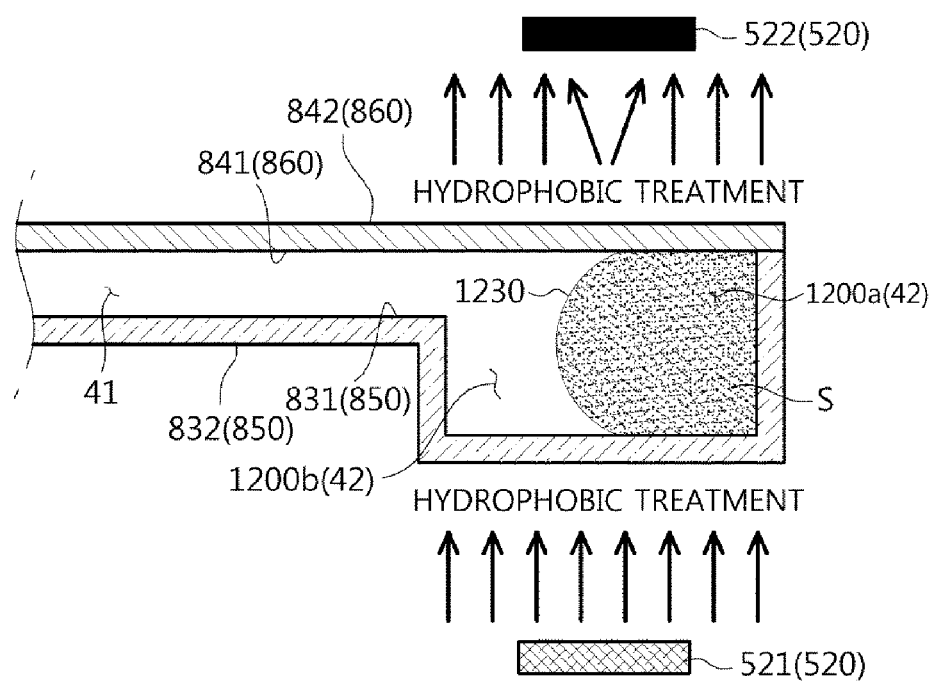

As illustrated in FIG. 16B, when all of the first surface 831 of the first plate 850 and the second surface 841 of the second plate 860 forming the excess sample chamber 1200 are treated by a hydrophobic treatment, a boundary surface 1230 may be formed in a convex shape with respect to a sample.

Figure 16C:
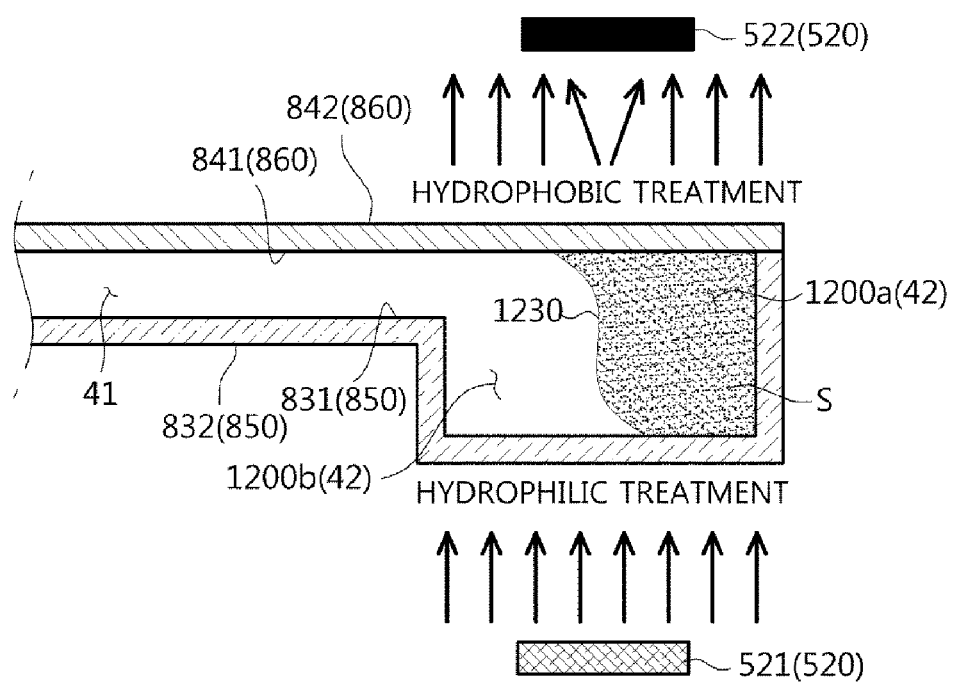

As illustrated in FIG. 16C, when the first surface 831 of the first plate 850 is treated by a hydrophilic treatment and the second surface 841 of the second plate 860 forming the excess sample chamber 1200 is treated by a hydrophobic treatment, a boundary surface 1230 having an inflection point may be formed. In other words, a portion of the boundary surface 1230 adjacent to the first surface 831 may be concave with respect to the sample and the other portion of the boundary surface 1230 adjacent to the second surface 841 may be convex with respect to the sample.

Figure 16D:
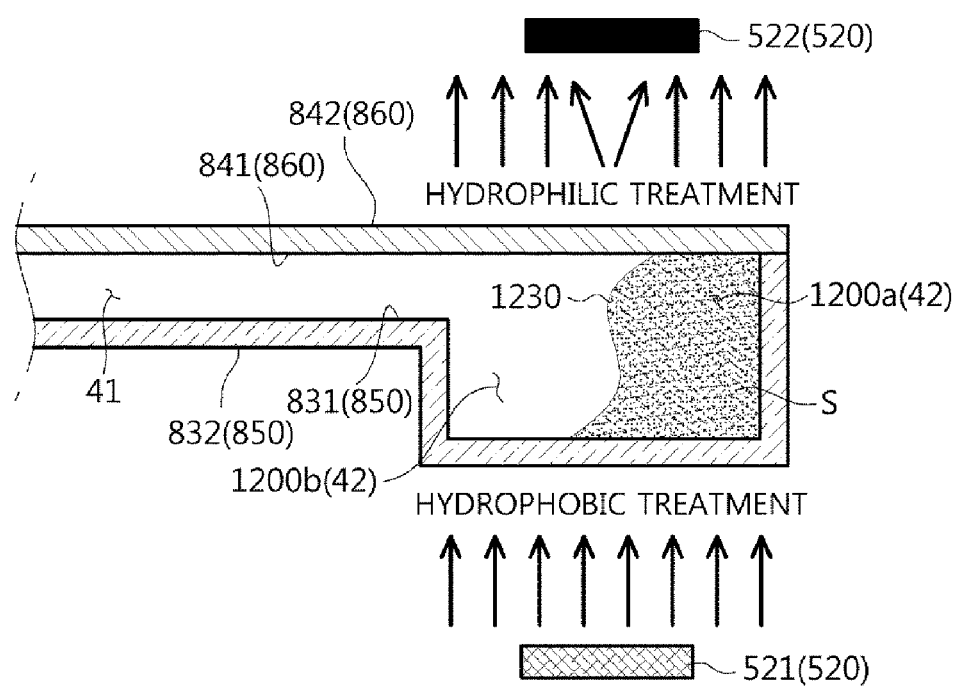

As illustrated in FIG. 16D, when the first surface 831 of the first plate 850 is treated by a hydrophobic treatment and the second surface 841 of the second plate 860 forming the excess sample chamber 1200 is treated by a hydrophilic treatment, a boundary surface 1230 having an inflection point may be formed. In other words, a portion of the boundary surface 1230 adjacent to the first surface 831 may be convex with respect to the sample and the other portion of the boundary surface 1230 adjacent to the second surface 841 may be concave with respect to the sample.

As illustrated in FIGS. 16C and 16D, when the first surface 831 and the second surface 841 are treated by treatments different from each other to thereby make the first surface 831 and second surface 841 different types of hydrophilic or hydrophobic material, an amount of light reflected or refracted on the boundary surface 1230 may be maximized so that the discrimination of the optical density of the excess sample chamber 1200 depending on the presence of the sample may be improved to a greater degree.

The detection device 520 may include at least one of a photodiode and a recording device. For example, flash lighting may be used as the light emitting unit 521 of the detection device 520, and a recording device, such as a camera, may be used as the light receiving unit 522 of the detection device 520. In this case, by imaging the excess sample chamber 1200, whether a sample is injected into the excess sample chamber 120 may be determined based on the presence of the boundary surface 1230 between a sample and air.

Hereinafter a method of detecting a sample to determine whether a sample supplied to the microfluidic device is supplied in an appropriate amount will be described.

The method of detecting a sample to determine whether an amount of a sample supplied to the microfluidic device is appropriate may include injecting a sample into the sample chamber 10, moving the sample injected into the sample chamber 10 to the sample distribution chambers 31 and 32, moving the rest of the sample, which is remaining after filling the sample distribution chambers 31 and 32, to the excess sample chamber 1200, moving a part of the sample moved to the excess sample chamber 120 to the sample accommodation unit 1210 so that a portion of the excess sample chamber 1200 is filled with air and the other portion of the excess sample chamber is filled with a sample, and measuring the optical density of the excess sample chamber 1200 by using the detection device 520.

As is apparent from the above description, according to the proposed microfluidic device and a method of detecting a sample supplied to the same, by placing a boundary surface, which is formed between a sample and air accommodated in the excess sample chamber, on a light transmission path where light emitted from the light emitting unit of the detection device is transmitted to the light receiving unit of the detection device, it may be easily confirmed whether a sample is present in the excess sample chamber.

In addition, by providing a dye in the excess sample chamber, the difference of the optical density of the excess sample chamber depending on the presence of a sample may be clearly determined, wherein the sample has an excellent transparency.

By forming a structure configured to induce the change of the progress direction of the light, which is emitted from the light emitting unit of the detection device and transmitted to the light receiving unit of the detection device, the difference of the optical density of the excess sample chamber depending on the presence of a sample may be apparent regardless of the type of the sample.

By applying at least one of a hydrophilic treatment and a hydrophobic treatment to the inner surface of the excess sample chamber, the difference of the optical density of the excess sample chamber depending on the presence of a sample may be made apparent.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. A method of detecting a sample to determine whether an amount of the sample supplied to a microfluidic device is appropriate, the method comprising:
    filling a sample distribution chamber with the sample;
    moving a remaining portion of the sample, which is remaining after the filling of the sample distribution chamber with the sample, to an excess sample chamber;
    moving a part of the remaining portion of the sample moved to the excess sample chamber to a sample accommodating chamber so that a portion of the excess sample chamber is filled with the sample and a remaining portion of the excess sample chamber is filled with air; and
    measuring an optical density of the excess sample chamber by using a detection device.

2. The method of claim 1, wherein the moving of the part of the remaining portion of the sample moved to the excess sample chamber to the sample accommodating chamber comprises:
    moving the part of the remaining portion of the sample to the sample accommodating chamber through an excess sample moving channel connected to the excess sample chamber and the sample accommodating chamber.

3. The method of claim 1, further comprising:
    dyeing the sample introduced into the excess sample chamber.

4. The method of claim 1, wherein in the measuring the optical density of the excess sample chamber, a boundary between the sample and the air in the excess sample chamber is detected.

5. The method of claim 4, wherein the measuring comprises:
- emitting, by a light emitter included in the detection device, light towards the excess sample chamber on a light transmission path;
- receiving, by a light receiver included in the detection device, the light; and
- measuring the optical density of the excess sample chamber based on the received light.

6. The method of claim 5, wherein:
the boundary between the remaining portion of the sample and the air accommodated in the excess sample chamber is provided on the light transmission path.

7. The method of claim 5, wherein:
the excess sample chamber comprises:
- a first plate facing the light emitter, and
- a second plate facing the light receiver, wherein the first plate and the second plate comprise one of a hydrophilic material and a hydrophobic material.

8. The method of claim 1, wherein in the measuring the optical density of the excess sample chamber, an amount of the sample in the excess sample chamber is detected.

* * * * *